(12) United States Patent
Messing et al.

(10) Patent No.: US 9,909,134 B2
(45) Date of Patent: Mar. 6, 2018

(54) RNA-SEQ TRANSCRIPTOME ANALYSIS OF SPIRODELA DORMANCY WITHOUT REPRODUCTION AND IDENTIFICATION OF MOLECULAR TARGETS USEFUL FOR IMPROVING BIOMASS PRODUCTION FOR INDUSTRIAL APPLICATIONS

(71) Applicant: RUTGERS, THE STATE UNIVERSITY OF NEW JERSEY, New Brunswick, NJ (US)

(72) Inventors: Joachim Messing, Somerset, NJ (US); Wenqin Wang, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 267 days.

(21) Appl. No.: 14/562,312

(22) Filed: Dec. 5, 2014

(65) Prior Publication Data
US 2015/0159165 A1 Jun. 11, 2015

Related U.S. Application Data

(60) Provisional application No. 61/912,328, filed on Dec. 5, 2013.

(51) Int. Cl.
*C12N 15/82* (2006.01)

(52) U.S. Cl.
CPC ..... *C12N 15/8247* (2013.01); *C12N 15/8218* (2013.01); *C12N 15/8245* (2013.01)

(58) Field of Classification Search
None
See application file for complete search history.

(56) References Cited

U.S. PATENT DOCUMENTS

2010/0317073 A1* 12/2010 Sayre .................... C10G 1/00
435/136

OTHER PUBLICATIONS

Wang et al, 2012, BMC Plant Biology, 12:1-14.*
Fritzius et al, 2001, Plant Physiology, 126:883-889.*
Yan et al, 2013, BMC Plant Biology, 13:1-13.*
Sanjaya et al, 2011, Plant Biotechnology, 9:874-883.*
Miki et al, 2005, Plant Physiology, 138:1903-1913.*
Alkan et al., Limitations of next-generation genome sequence assembly, Nat Methods, 2011, 8(1), 61-65.
Appenroth et al., Telling duckweed apart: genotyping technologies for the Lemnaceae, Chin J Appl Environ Biol, 2013, 19(1), 1-10.
Appenroth et al. Turion formation in Spirodela polyrhiza: The environmental signals that induce the developmental process in nature, Physiologia plantarum, 2009, 138(3), 312-320.
Appenroth et al., Co-action of temperature and phosphate in inducing turion formation in *Spirodela polyrhiza* (Great duckweed), Plant, Cell & Environment, 2002, 25(9), 1079-1085.

*Arabidopsis*-Consortium, Analysis of the genome sequence of the flowering plant *Arabidopsis thaliana*, Nature, 2000, 408(6814), 796-815.
Brachypodium-Consortium, Genome sequencing and analysis of the model grass *Brachypodium distachyon*, Nature, 2010, 463(7282), 763-768.
Brain et al., A protocol for conducting 7-day daily renewal tests with Lemna gibba, Nat Protoc, 2007, 2(4), 979-987.
Cao et al., Whole-genome sequencing of multiple *Arabidopsis thaliana* populations, Nat Genet, 2011, 43(10), 956-963.
Cheng et al., Nutrient recovery from swine lagoon water by Spirodela punctata, Bioresource Technology, 2002, 81(1), 81-85.
Cheng et al., Growing duckweed to recover nutrients from wastewaters and for production of fuel ethanol and animal feed, CLEAN—Soil, Air, Water, 2009, 37(1), 17-26.
Cronn et al., Multiplex sequencing of plant chloroplast genomes using Solexa sequencing-by-synthesis technology, Nucleic Acids Res., 2008, 36(19), e122-e122.
D'Hont et al., The banana (*Musa acuminata*) genome and the evolution of monocotyledonous plants, Nature, 2012, 488(7410), 213-217.
Gardner et al., The complete nucleotide sequence of an infectious clone of cauliflower mosaic virus by M13mp7 shotgun sequencing, Nucleic Acids Res, 1981, 9(12), 2871-2888.
Hollingsworth et al., Selecting barcoding loci for plants: evaluation of seven candidate loci with species-level sampling in three divergent groups of land plants, Mol Ecol Resour, 2009, 9(2), 439-457.
Huang et al., The genome of the cucumber, *Cucumis sativus* L, Nat Genet, 2009, 41(12), 1275-1281.
Wang et al., RNA-Seq transcriptome analysis of Spirodela dormancy without reproduction, BMC Genomics, 2014b, 15(1), 60.
Ko et al., Expression of the protective antigen for PEDV in transgenic duckweed, *Lemna minor*, Horticulture, Environment, and Biotechnology, 2011, 52(5), 511-515.
Kuehdorf et al., The clonal dependence of turion formation in the duckweed *Spirodela polyrhiza*—an ecogeographical approach, Physiol Plant, 2014, 150(1), 46-54.
Yan et al., Survey of the total fatty acid and triacylglycerol composition and content of 30 duckweed species and cloning of a Delta6-desaturase responsible for the production of gamma-linolenic and stearidonic acids in Lemna gibba, BMC Plant Biol, 2013, 13, 201.
Yamamoto et al., Genetic transformation of duckweed *Lemna gibba* and *Lemna minor* In Vitro Cellular & Developmental Biology, Plant, 2000, 37, 349-353.
Les et al., Systematics of theLemnaceae (duckweeds): Inferences from micromolecular and morphological data. Plant Systematics and Evolution, 1997, 204(3-4), 161-177.
Les et al., Phylogeny and Systematics of Lemnaceae, the Duckweed Family. Systematic Botany, 2002, 27(2), 221-240.
Luo et al., High-throughput fingerprinting of bacterial artificial chromosomes using the snapshot labeling kit and sizing of restriction fragments by capillary electrophoresis, Genomics, 2003, 82(3), 378-389.
Mardanov et al., Complete sequence of the duckweed (*Lemna minor*) chloroplast genome: structural organization and phylogenetic relationships to other angiosperms, Journal of Molecular Evolution, 2008, 66(6), 555-564.
Metzker et al., Sequencing technologies—the next generation, Nat Rev Genet, 2010, 11(1), 31-46.
Ozengin et al., Performance of duckweed (*Lemna minor* L.) on different types of wastewater treatment, J Environ Biol, 2007, 28(2), 307-314.

(Continued)

Primary Examiner — Jason Deveau Rosen
(74) Attorney, Agent, or Firm — Kathleen D. Rigaut; Dann, Dorfman, Herrell & Skillman

(57) ABSTRACT

Compositions and methods are provided for altering carbon partitioning in biomass isolated from Duckweed.

10 Claims, 6 Drawing Sheets

(56) References Cited

OTHER PUBLICATIONS

Paterson et al., The Sorghum bicolor genome and the diversification of grasses, Nature, 2009, 457(7229), 551-556.
Rice-Consortium, The map-based sequence of the rice genome, Nature, 2005, 436(7052), 793-800.
Rusoff et al., Duckweeds (Lemnaceae family): a potential source of protein and amino acids. Journal of Agricultural and Food Chemistry, 1980, 28(4), 848-850.
Sanger et al., Nucleotide sequence of bacteriophage phi X174 DNA, Nature, 1997, 265(5596), 687-695.
Schnable et al., The B73 maize genome: complexity, diversity, and dynamics, Science, 2009, 326(5956), 1112-1115.
Wang et al., DNA barcoding of the Lemnaceae, a family of aquatic monocots, BMC Plant Biology, 2010, 10, 205.
Sun et al., Expression and characterization of Acidothermus cellulolyticus E1 endoglucanase in transgenic duckweed *Lemna minor* 8627, Bioresour Technol, 2007, 98(15), 2866-2872.
Tao et al., Comparative transcriptome analysis to investigate the high starch accumulation of duckweed (*Landoltia punctata*) under nutrient starvation, Biotechnol Biofuels, 2013, 6(1), 72.
Vunsh et al., High expression of transgene protein in Spirodela, Plant Cell Reports, 2007, 26(9), 1511-1519.
Wang, W., The Spirodela polyrhiza genome reveals insights into its neotenous reduction, fast growth and aquatic lifestyle, Nature Communications, 2014a, 5, 3311.
Wang et al., Analysis of ADP-glucose pyrophosphorylase expression during turion formation induced by abscisic acid in *Spirodela polyrhiza* (greater duckweed), BMC Plant Biology, 2012, 12(1), 5.
Wang et al., The mitochondrial genome of an aquatic plant, Spirodela polyrhiza. PLoS ONE, 2012, 7(10), e46747.
Jones et al., Using RNA-Seq to profile soybean seed development from fertilization to maturity, PLoS One, 2013, 8(3), e59270.
Liu et al., Regulation of wheat seed dormancy by after-ripening is mediated by specific transcriptional switches that induce changes in seed hormone metabolism and signaling, PLoS One 2013, 8(2), e56570.
Ueno et al., Transcriptional profiling of bud dormancy induction and release in oak by next-generation sequencing, BMC Genomics, 2013, 14, 236.
Appenroth et al., Turion formation in Spirodela polyrhiza: The environmental signals that induce the developmental process in nature, Physiologia Plantarum, 2009, 138(3), 312-320.
Appenroth et al., Photophysiology of turion formation and germination in Spirodela polyrhiza, Biologia Plantarum 1996, 38(1), 95-106.
Appenroth et al., Appenroth KJ, Ziegler P: Light-induced degradation of storage starch in turions of Spirodela polyrhiza depends on nitrate, Plant Cell Environ, 2008, 31(10), 1460-1469.
Appenroth et al., Light-induced degradation of starch granules in turions of Spirodela polyrhiza studied by electron microscopy, Plant Cell Physiol, 2011, 52(2), 384-391.
Wang et al., High-Throughput Sequencing of Three Lemnoideae (Duckweeds) Chloroplast Genomes from Total DNA, PLoS ONE, 2011, 6(9):e24670.
Smart et al., Abscisic-acid-induced turion formation in Spirodela polyrrhiza L. II. Ultrastructure of the turion; a stereological analysis. Plant, Cell and Environment, 1983, 6(6), 515-522.
Smart et al., Abscisic-acid-induced turion formation in Spirodela polyrrhiza L. I. Production and development of the turion, Plant, Cell and Environment, 1983, 6(6), 507-514.
Smart et al., The physiological role of abscisic acid in eliciting turion morphogenesis, Plant Physiol 1995, 108(2), 623-632.
Wu et al., Y, Messing J: RNA interference-mediated change in protein body morphology and seed opacity through loss of different zein proteins, Plant Physiol, 2010, 153(1):337-347.

* cited by examiner

Figure 1
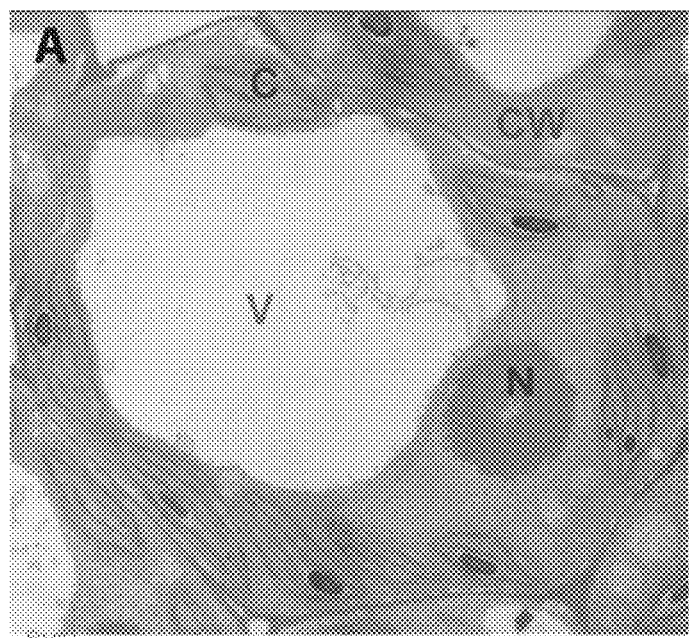
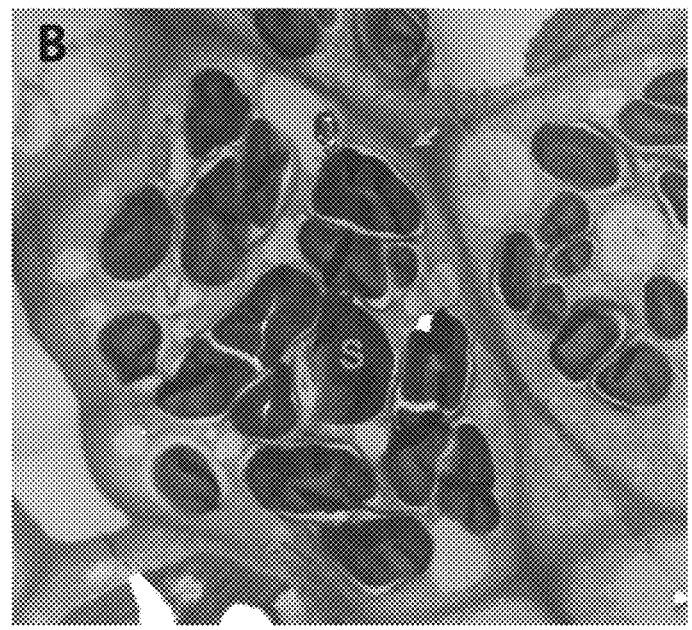

SEQUENCE LISTING

```
<160> NUMBER OF SEQ ID NOS: 37

<210> SEQ ID NO 1
<211> LENGTH: 10
<212> TYPE: PRT
<213> ORGANISM: Spirodela polyrhiza

<400> SEQUENCE: 1

Gln Lys Thr Val Asp Glu Val Trp Arg Asp
1               5                   10

<210> SEQ ID NO 2
<211> LENGTH: 10
<212> TYPE: PRT
<213> ORGANISM: Spirodela polyrhiza

<400> SEQUENCE: 2

Arg Arg Thr Ala Glu Gly Glu Trp Lys Asn
1               5                   10

<210> SEQ ID NO 3
<211> LENGTH: 10
<212> TYPE: PRT
<213> ORGANISM: Spirodela polyrhiza

<400> SEQUENCE: 3

Gln Lys Thr Val Asp Glu Val Trp Arg Asp
1               5                   10

<210> SEQ ID NO 4
<211> LENGTH: 10
<212> TYPE: PRT
<213> ORGANISM: Spirodela polyrhiza

<400> SEQUENCE: 4

Arg Arg Thr Ala Glu Glu Val Trp Glu Glu
1               5                   10

<210> SEQ ID NO 5
```

```
<211> LENGTH: 10
<212> TYPE: PRT
<213> ORGANISM: Spirodela polyrhiza

<400> SEQUENCE: 5

Arg Lys Thr Val Asp Glu Val Trp Ser Glu
 1               5                  10

<210> SEQ ID NO 6
<211> LENGTH: 10
<212> TYPE: PRT
<213> ORGANISM: Spirodela polyrhiza

<400> SEQUENCE: 6

Lys Lys Thr Val Asp Glu Val Trp Leu Asp
 1               5                  10

<210> SEQ ID NO 7
<211> LENGTH: 10
<212> TYPE: PRT
<213> ORGANISM: Spirodela polyrhiza

<400> SEQUENCE: 7

Arg Lys Thr Val Glu Glu Val Trp Ser Asp
 1               5                  10

<210> SEQ ID NO 8
<211> LENGTH: 10
<212> TYPE: PRT
<213> ORGANISM: Spirodela polyrhiza

<400> SEQUENCE: 8

Arg Arg Gly Glu Asp Asp Glu Val Ala Glu
 1               5                  10

<210> SEQ ID NO 9
<211> LENGTH: 6
<212> TYPE: PRT
<213> ORGANISM: Artificial Sequence
<220> FEATURE:
<223> OTHER INFORMATION: Consensus motif 1 sequence

<400> SEQUENCE: 9

Thr Val Asp Glu Val Trp
 1               5

<210> SEQ ID NO 10
<211> LENGTH: 17
<212> TYPE: PRT
<213> ORGANISM: Spirodela polyrhiza

<400> SEQUENCE: 10

Thr Leu Gly Glu Ile Thr Leu Glu Glu Phe Leu Leu Arg Ala Gly Leu
 1               5                  10                  15

Val

<210> SEQ ID NO 11
<211> LENGTH: 17
<212> TYPE: PRT
<213> ORGANISM: Spirodela polyrhiza

<400> SEQUENCE: 11

Ala Val Glu Gly Met Thr Leu Glu Asp Phe Leu Ser Met Glu Val Val
 1               5                  10                  15
```

Thr

```
<210> SEQ ID NO 12
<211> LENGTH: 17
<212> TYPE: PRT
<213> ORGANISM: Spirodela polyrhiza

<400> SEQUENCE: 12
```

Thr Met Gly Glu Ile Thr Leu Glu Glu Phe Leu Leu Lys Ala Gly Val
 1               5                  10                  15

Val

```
<210> SEQ ID NO 13
<211> LENGTH: 17
<212> TYPE: PRT
<213> ORGANISM: Spirodela polyrhiza

<400> SEQUENCE: 13
```

Glu Phe Glu Asn Ile Thr Leu Glu Asp Phe Leu Ala Arg Ala Gly Ala
 1               5                  10                  15

Val

```
<210> SEQ ID NO 14
<211> LENGTH: 17
<212> TYPE: PRT
<213> ORGANISM: Spirodela polyrhiza

<400> SEQUENCE: 14
```

Thr Phe Gly Glu Met Thr Leu Glu Asp Phe Leu Ile Lys Ala Gly Val
 1               5                  10                  15

Val

```
<210> SEQ ID NO 15
<211> LENGTH: 17
<212> TYPE: PRT
<213> ORGANISM: Spirodela polyrhiza

<400> SEQUENCE: 15
```

Thr Leu Gly Glu Met Thr Leu Glu Asp Phe Leu Val Lys Ala Gly Val
 1               5                  10                  15

Val

```
<210> SEQ ID NO 16
<211> LENGTH: 17
<212> TYPE: PRT
<213> ORGANISM: Spirodela polyrhiza

<400> SEQUENCE: 16
```

Thr Phe Gly Glu Met Thr Leu Glu Asp Phe Leu Val Lys Ala Gly Val
 1               5                  10                  15

Val

```
<210> SEQ ID NO 17
<211> LENGTH: 19
<212> TYPE: PRT
<213> ORGANISM: Spirodela polyrhiza

<400> SEQUENCE: 17
```

Ala Gly Gly Arg Leu Ser Ser Ile Pro Glu Asp Thr Asp Gln Tyr His
 1               5                  10                  15

Glu Tyr Leu

-continued

```
<210> SEQ ID NO 18
<211> LENGTH: 6
<212> TYPE: PRT
<213> ORGANISM: Artificial Sequence
<220> FEATURE:
<223> OTHER INFORMATION: Consensus motif 2 sequence

<400> SEQUENCE: 18

Thr Leu Glu Asp Phe Leu
1               5

<210> SEQ ID NO 19
<211> LENGTH: 37
<212> TYPE: PRT
<213> ORGANISM: Spirodela polyrhiza

<400> SEQUENCE: 19

Arg Met Ile Lys Asn Arg Glu Ser Ala Ala Arg Ser Arg Ala Arg Lys
1               5                   10                  15

Gln Ala Tyr Thr Met Glu Leu Glu Ala Glu Ile Thr Lys Leu Lys Glu
            20                  25                  30

Gln Asn Glu Leu Leu
        35

<210> SEQ ID NO 20
<211> LENGTH: 37
<212> TYPE: PRT
<213> ORGANISM: Spirodela polyrhiza

<400> SEQUENCE: 20

Arg Met Met Lys Asn Arg Glu Ser Ala Ala Arg Ser Arg Ala Arg Lys
1               5                   10                  15

Gln Ala Tyr Thr Asn Glu Leu Glu Asn Lys Ile Ser Arg Leu Glu Glu
            20                  25                  30

Glu Asn Glu Arg Leu
        35

<210> SEQ ID NO 21
<211> LENGTH: 37
<212> TYPE: PRT
<213> ORGANISM: Spirodela polyrhiza

<400> SEQUENCE: 21

Arg Met Ile Lys Asn Arg Glu Ser Ala Ala Arg Ser Arg Ala Arg Lys
1               5                   10                  15

Gln Ala Tyr Thr Leu Glu Leu Glu Ala Glu Ile Ala Lys Leu Lys Glu
            20                  25                  30

Gln Asn Glu Glu Leu
        35

<210> SEQ ID NO 22
<211> LENGTH: 37
<212> TYPE: PRT
<213> ORGANISM: Spirodela polyrhiza

<400> SEQUENCE: 22

Arg Met Ile Lys Asn Arg Glu Ser Ala Ala Arg Ser Arg Glu Arg Lys
1               5                   10                  15

Gln Ala Tyr Ile Gln Gln Leu Glu Thr Leu Ala Ala Arg Leu Glu Glu
            20                  25                  30
```

-continued

Glu Asn Ala Thr Leu
        35

<210> SEQ ID NO 23
<211> LENGTH: 37
<212> TYPE: PRT
<213> ORGANISM: Spirodela polyrhiza

<400> SEQUENCE: 23

Arg Met Ile Lys Asn Arg Glu Ser Ala Ala Arg Ser Arg Ala Arg Lys
 1               5                  10                  15

Gln Ala Tyr Thr Val Glu Leu Glu Thr Glu Leu Asn Gln Leu Lys Glu
            20                  25                  30

Glu Asn Ala Arg Leu
        35

<210> SEQ ID NO 24
<211> LENGTH: 37
<212> TYPE: PRT
<213> ORGANISM: Spirodela polyrhiza

<400> SEQUENCE: 24

Arg Met Ile Lys Asn Arg Glu Ser Ala Ala Arg Ser Arg Ala Arg Lys
 1               5                  10                  15

Gln Ala Tyr Thr Asn Glu Leu Glu Asn Lys Val Ser Arg Leu Glu Glu
            20                  25                  30

Glu Asn Lys Met Leu
        35

<210> SEQ ID NO 25
<211> LENGTH: 37
<212> TYPE: PRT
<213> ORGANISM: Spirodela polyrhiza

<400> SEQUENCE: 25

Arg Met Met Lys Asn Arg Glu Ser Ala Ala Arg Ser Arg Ala Arg Lys
 1               5                  10                  15

Gln Ala Tyr Thr Val Glu Leu Glu Lys Glu Leu Thr Phe Leu Lys Glu
            20                  25                  30

Glu Asn Ala Arg Leu
        35

<210> SEQ ID NO 26
<211> LENGTH: 37
<212> TYPE: PRT
<213> ORGANISM: Spirodela polyrhiza

<400> SEQUENCE: 26

Arg Met Leu Ser Asn Arg Glu Ser Ala Arg Arg Ser Arg Lys Arg Lys
 1               5                  10                  15

Gln Ala His Leu Ser Glu Leu Glu Ala Gln Val Ser Gln Leu Arg Ala
            20                  25                  30

Glu Asn Ser Ser Leu
        35

<210> SEQ ID NO 27
<211> LENGTH: 33
<212> TYPE: PRT
<213> ORGANISM: Artificial Sequence
<220> FEATURE:
<223> OTHER INFORMATION: Consensus bZIP sequence
<220> FEATURE:

```
<221> NAME/KEY: VARIANT
<222> LOCATION: 2-8, 10-18, 20-25, 27-32
<223> OTHER INFORMATION: Xaa = ant amino acid

<400> SEQUENCE: 27

Asn Xaa Xaa Xaa Xaa Xaa Xaa Arg Xaa Xaa Xaa Xaa Xaa Xaa
 1               5                  10

Xaa Xaa Leu Xaa Xaa Xaa Xaa Xaa Leu Xaa Xaa Xaa Xaa Xaa
             20                  25                  30

Leu

<210> SEQ ID NO 28
<211> LENGTH: 58
<212> TYPE: PRT
<213> ORGANISM: Arabidopsis thaliana

<400> SEQUENCE: 28

His Tyr Arg Gly Val Arg Gln Arg Pro Trp Gly Lys Phe Ala Ala Glu
 1               5                  10                  15

Ile Arg Asp Pro Ala Lys Asn Gly Ala Arg Val Trp Leu Gly Thr Phe
                 20                  25                  30

Glu Thr Ala Glu Asp Ala Ala Leu Ala Tyr Asp Arg Ala Ala Phe Arg
             35                  40                  45

Met Arg Gly Ser Arg Ala Leu Leu Asn Phe
         50                  55

<210> SEQ ID NO 29
<211> LENGTH: 58
<212> TYPE: PRT
<213> ORGANISM: Arabidopsis thaliana

<400> SEQUENCE: 29

His Tyr Arg Gly Val Arg Gln Arg Pro Trp Gly Lys Phe Ala Ala Glu
 1               5                  10                  15

Ile Arg Asp Pro Ala Lys Asn Gly Ala Arg Val Trp Leu Gly Thr Phe
                 20                  25                  30

Glu Thr Ala Glu Asp Ala Ala Leu Ala Tyr Asp Ile Ala Ala Phe Arg
             35                  40                  45

Met Arg Gly Ser Arg Ala Leu Leu Asn Phe
         50                  55

<210> SEQ ID NO 30
<211> LENGTH: 57
<212> TYPE: PRT
<213> ORGANISM: Arabidopsis thaliana

<400> SEQUENCE: 30

Arg Phe Arg Gly Val Arg Lys Arg Pro Trp Gly Arg Phe Ala Ala Glu
 1               5                  10                  15

Ile Arg Asp Pro Trp Lys Lys Ala Arg Val Trp Leu Gly Thr Phe Asp
                 20                  25                  30

Ser Ala Glu Glu Ala Ala Arg Ala Tyr Asp Ser Ala Ala Arg Asn Leu
             35                  40                  45

Arg Gly Pro Lys Ala Lys Thr Asn Phe
         50                  55

<210> SEQ ID NO 31
<211> LENGTH: 57
<212> TYPE: PRT
<213> ORGANISM: Arabidopsis thaliana
```

<400> SEQUENCE: 31

Arg Tyr Arg Gly Val Arg Lys Arg Pro Trp Gly Arg Tyr Ala Ala Glu
 1               5                  10                  15

Ile Arg Asp Pro Gly Lys Lys Thr Arg Val Trp Leu Gly Thr Phe Asp
            20                  25                  30

Thr Ala Glu Glu Ala Ala Arg Ala Tyr Asp Thr Ala Ala Arg Asp Phe
        35                  40                  45

Arg Gly Ala Lys Ala Lys Thr Asn Phe
    50                  55

<210> SEQ ID NO 32
<211> LENGTH: 58
<212> TYPE: PRT
<213> ORGANISM: Arabidopsis thaliana

<400> SEQUENCE: 32

His Tyr Arg Gly Val Arg Gln Arg Pro Trp Gly Lys Phe Ala Ala Glu
 1               5                  10                  15

Ile Arg Asp Pro Asn Lys Arg Gly Ser Arg Val Trp Leu Gly Thr Phe
            20                  25                  30

Asp Thr Ala Ile Glu Ala Ala Arg Ala Tyr Asp Glu Ala Ala Phe Arg
        35                  40                  45

Leu Arg Gly Ser Lys Ala Ile Leu Asn Phe
    50                  55

<210> SEQ ID NO 33
<211> LENGTH: 58
<212> TYPE: PRT
<213> ORGANISM: Spirodela polyrhiza

<400> SEQUENCE: 33

Cys Tyr Arg Gly Val Arg Lys Arg Pro Trp Gly Lys Phe Ala Ala Glu
 1               5                  10                  15

Ile Arg Asp Ser Thr Arg His Gly Arg Arg Val Trp Leu Gly Thr Phe
            20                  25                  30

Asp Ser Pro Glu Ala Ala Ala Leu Ala Tyr Asp Gln Ala Ala Phe Ala
        35                  40                  45

Thr Arg Gly Ala Leu Ala Val Leu Asn Phe
    50                  55

<210> SEQ ID NO 34
<211> LENGTH: 57
<212> TYPE: PRT
<213> ORGANISM: Spirodela polyrhiza

<400> SEQUENCE: 34

Leu Tyr Arg Gly Ile Arg Arg Arg Pro Trp Gly Lys Trp Ala Ala Glu
 1               5                  10                  15

Ile Arg Asp Pro Met Lys Gly Val Arg Val Trp Leu Gly Thr Tyr Gln
            20                  25                  30

Ser Pro Glu Glu Ala Ala Arg Ala Tyr Asp Arg Ala Ala Arg Arg Ile
        35                  40                  45

Arg Gly Ser Lys Ala Lys Leu Asn Phe
    50                  55

<210> SEQ ID NO 35
<211> LENGTH: 57
<212> TYPE: PRT

```
<213> ORGANISM: Spirodela polyrhiza

<400> SEQUENCE: 35

Leu Tyr Arg Gly Val Arg Gln Arg His Trp Gly Lys Trp Val Ala Glu
 1               5                  10                  15

Ile Arg Leu Pro Arg Asn Arg Thr Arg Leu Trp Leu Gly Thr Phe Asp
            20                  25                  30

Thr Ala Met Glu Ala Ala Met Ala Tyr Asp Asp Ala Ala Phe Lys Leu
        35                  40                  45

Arg Gly Glu Leu Ala Arg Leu Asn Phe
    50                  55

<210> SEQ ID NO 36
<211> LENGTH: 57
<212> TYPE: PRT
<213> ORGANISM: Spirodela polyrhiza

<400> SEQUENCE: 36

Val Tyr Arg Gly Val Arg Arg Arg Ser Ala Gly Lys Trp Val Cys Glu
 1               5                  10                  15

Val Arg Glu Pro Asn Lys Lys Ser Arg Ile Trp Leu Gly Thr Phe Pro
            20                  25                  30

Thr Ala Glu Met Ala Ala Arg Ala His Asp Val Ala Ala Met Ala Leu
        35                  40                  45

Arg Gly Arg Ser Ala Cys Leu Asn Phe
    50                  55

<210> SEQ ID NO 37
<211> LENGTH: 58
<212> TYPE: PRT
<213> ORGANISM: Artificial Sequence
<220> FEATURE:
<223> OTHER INFORMATION: Consensus ERF domain sequence
<220> FEATURE:
<221> NAME/KEY: VARIANT
<222> LOCATION: 1, 7, 13, 21, 23, 25, 33, 40, 44, 47-49, 52, 55
<223> OTHER INFORMATION: Xaa = any amino acid

<400> SEQUENCE: 37

Xaa Tyr Arg Gly Val Arg Xaa Arg Pro Trp Gly Lys Xaa Ala Ala Glu
 1               5                  10                  15

Ile Arg Asp Pro Xaa Lys Xaa Gly Xaa Arg Val Trp Leu Gly Thr Phe
            20                  25                  30

Xaa Thr Ala Glu Glu Ala Ala Xaa Ala Tyr Asp Xaa Ala Ala Xaa Xaa
        35                  40                  45

Xaa Arg Gly Xaa Lys Ala Xaa Leu Asn Phe
    50                  55
```

RNA-SEQ TRANSCRIPTOME ANALYSIS OF SPIRODELA DORMANCY WITHOUT REPRODUCTION AND IDENTIFICATION OF MOLECULAR TARGETS USEFUL FOR IMPROVING BIOMASS PRODUCTION FOR INDUSTRIAL APPLICATIONS

This application claims priority to U.S. Provisional Application No. 61/912,328 filed Dec. 5, 2013, the entire disclosure being incorporated herein by reference.

FIELD OF THE INVENTION

This invention relates to the fields of plant molecular biology and recombinant manipulation of plant species in order to maximize production of biomass having desirable characteristics. More specifically, the invention provides valuable gene targets for manipulating carbon production in Duckweed based on results obtained from deep sequencing of the Duckweed genome.

BACKGROUND OF THE INVENTION

Several publications and patent documents are referenced in this application in order to more fully describe the state of the art to which this invention pertains. Full citations for these references are found within and at the end of the specification. The disclosure of each of these references is incorporated by reference.

Plants, unlike animals, do not have fur nor can they seek shelter to survive under food shortage and cold weather conditions. Consequently, they often become dormant to avoid adverse environments, such as poor nutrition, chilling temperature and drought. Dormancy is a complex state of plant development, in which the plant body exhibits little or no growth. Plants resume their growth once the conditions are favorable.

There are mainly two types of plant dormancy, e.g., forming seeds or buds. Seed dormancy has been observed for many plants species including our major crops [1-3]. Winter dormant buds are found for instance in woody plants, bulbs, rhizomes and tubers of herbaceous plants [4]. Studies on the molecular mechanisms of bud dormancy transitions in perennial woody plants have been conducted, including pear[5], oak[6], and poplar[7].

*Spirodela polyrhiza*, a floating aquatic monocot, develops a specific dormant organ called a turion during its life cycle, which alternates between periods of clonal propagation and dormancy. Its leaf, stem and bud are extremely compact forming a round-shaped frond, resembling a single leaf. Large numbers of *Spirodela* plants can be maintained in cell cultures under totally controlled medium and environmental conditions. They reproduce vegetatively through budding of fronds (growth phase) during spring and summer[8] and transition to turions (dormant phase), when there is a shortage of nutrients in the fall or when the temperature drops in the winter[9].

Noticeably, fronds perform photosynthesis and turions function as storage for starch and germinate in the following spring[10-13]. Turion cells exhibit dense intercellular space, thick cell wall and are also rich in anthocyanins[14]. Therefore, turions provide a unique system to study both bud and seed dormancy because they reproduce like buds without sexual hybridization but are functionally equivalent to seeds that could generate a progeny plant in the growing season. Previous studies have shown that addition of abscisic acid (ABA) into growth medium quickly leads to turion formation after 5 days of treatment in the laboratory[13, 15, 16]. Only 3 days after ABA treatment, the *Spirodela* primordium is irreversibly committed to turion development[15]. The ease of growth and its direct contact with water make *Spirodela* a model system to gain molecular insights into plant dormancy[17].

At the molecular level, some studies on turion development have already been performed. For example, the transcript level of D-myo-inositol-3-phosphate synthase is rapidly induced within 15 min of ABA application, an enzyme that plays a key role in the inositol metabolism of the cell wall[18, 19]. The expression of the key enzyme ADP-glucose pyrophosphorylase (APL) for starch production[13] is significantly changed during turion formation. Still, not much information is known about the global transcriptome profiling for turion formation in this model system.

SUMMARY OF THE INVENTION

In accordance with the present invention, a method for altering carbon partitioning from starch to lipids in biomass produced from Duckweed cultures is disclosed. In one embodiment the method comprises introducing an agent or gene variant, which modulates expression of a gene product identified in Table S1, wherein the agent or gene variant is effective to reduce starch production and increase lipid production in said culture relative to control untreated or unaltered cultures. The agent may be a nucleic acid, a small molecule, an antibody or a chemical compound. In another embodiment, the promoters of genes with high expression levels identified in Tables S1 can either be used to overexpress coding regions of key enzymes in lipid biosynthesis or RNA interference products against transcripts of starch biosynthesis as they have been identified in Tables S1 or S2.

In one aspect of the method, the agent or gene variant inhibits or increases expression of at least one gene product identified in Table S1, the inhibition or increase resulting in increased lipid production in biomass obtained from said Duckweed culture.

In a preferred aspect of the inventive method the agent modulates, (e.g., inhibits or increases) expression of at least one gene selected from the group consisting of AGPS1, AGPL3, GBSSI, APL1, ACCase4, GPAT1, and DGAT2. Alternatively, the agent modulates production of at least one gene in Table S2, which shifts carbon partitioning, in turn increasing lipid and or protein biosynthesis.

In yet another aspect of the invention, a Duckweed plant produced from any of the methods described above is provided. In a particularly preferred embodiment, the Duckweed plant is *Spirodela polyrhiza*. Also encompassed by the present invention are plant parts, progeny, seed or cells obtained from the duckweed plants described herein.

BRIEF DESCRIPTION OF THE DRAWINGS

FIG. 1. Comparison between frond and mature turion by TEM. A. A frond cell with a big vacuole and well-shaped chloroplasts but few and less starch granules, Bar=2 µm; B. A turion cell with thick cell wall and abundant starch granules, Bar=2 µm; Abbreviation: cell wall (CW), chloroplast (C), starch granule (S), vacuole (V) and nucleus (N).

B. APL gene expression from RNA-Seq data. Abbreviation: APL1-JN180634; APL2-JN180635; APL3-JN180636.

Figure 4:
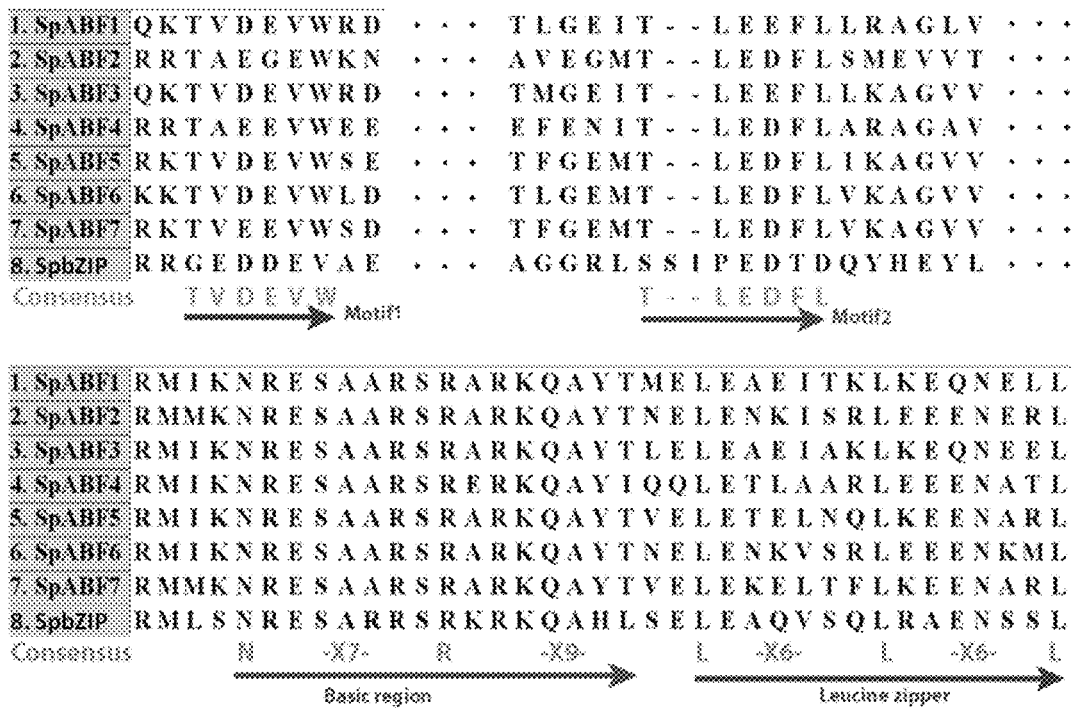

FIG. 4. Alignment of ABF domain from *Spirodela*. The amino acid sequences of bZIP protein sequence from *Spirodela* were aligned and the conserved regions were demonstrated here. The consensus amino acids were labeled from conserved regions and highlight as motif 1 and motif 2, the primary structure of bZIP domains (basic region and leucine zipper). All members contain these four domains except SpbZIP, which only has a basic region and a leucine zipper. SpABF1-Spipo4G0008600; SpABF2-Spipo6G0055300; SpABF3-Spipo15G0021000; SpABF4-Spipo4G0111500; SpABF5-Spipo7G0034500; SpABF6-Spipo3G0017700; SpABF7-Spipo13G0002500; SpbZIP-Spipo2G0055800. Motif 1 sequences are SEQ ID NOs: 1-9 from top to bottom, motif 2 sequences are SEQ ID NOs: 10-18 from top to bottom, bZIP domain sequences are SEQ ID NOs: 19-27.

Figure 5:
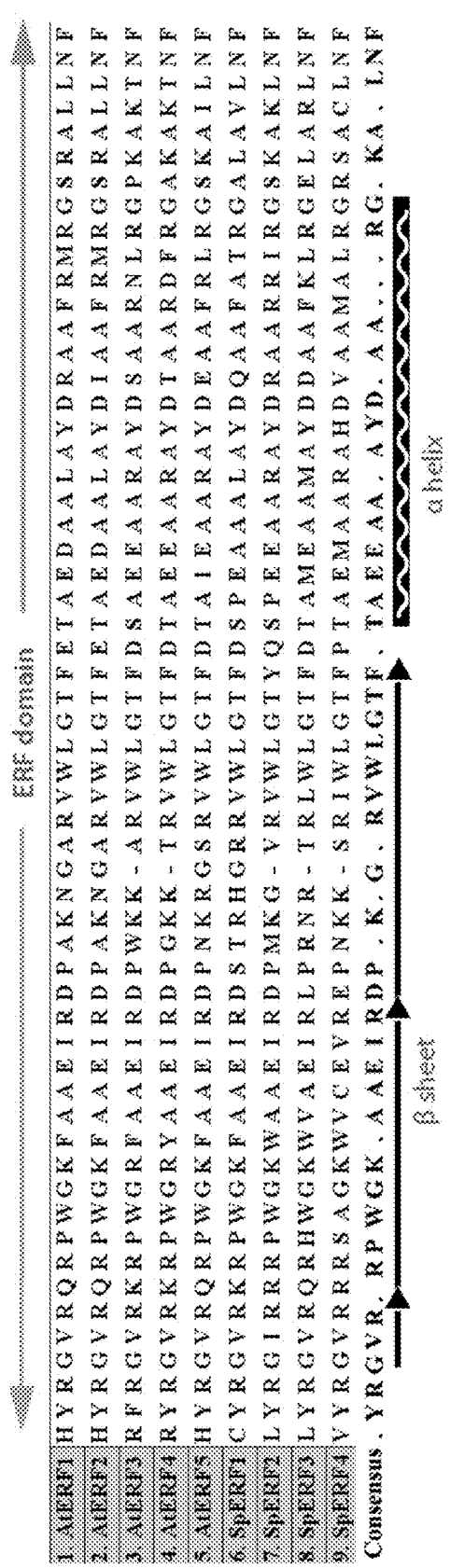

FIG. 5. Alignment of the ERF domain from *Arabidopsis* and *Spirodela*. The bar and black arrows indicate β sheet motif, which interacts with the GCC box of target DNA. The cross-hatched box indicates the a helix. The consensus amino acids are underlined in ERF domain. The accession numbers are: AtERF1-BAA32418; AtERF2-BAA32419; AtERF3-BAA32420; AtERF4-BAA32421; AtERF5-BAA32422; SpERF1-Spipo0G0155100; SpERF2-Spipo3G0031800; SpERF3-Spipo20G0027700; SpERF4-Spipo11G0028200. Sequences are SEQ ID NOs: 28-37, from top to bottom.

Figure 6:
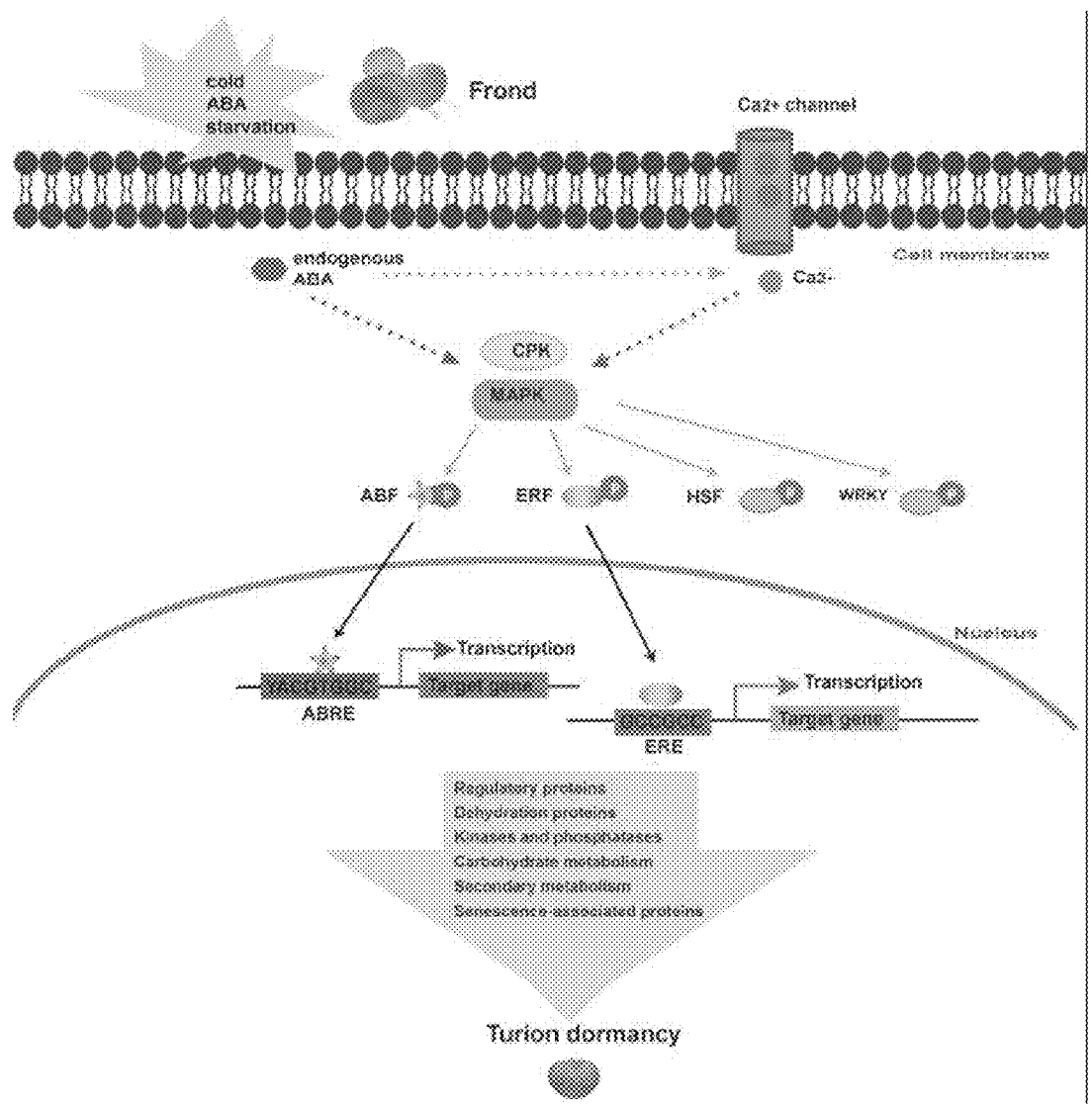

FIG. 6. A model of development of *Spirodela* dormancy through the signal transduction in response to environmental stimuli. Phosphorylated proteins are labeled as pink circles with a P inside. Solid lines represent direct connections. The dotted line indicates indirect connection. Not all linkages and details of pathway are shown in this diagram in order to simplify the model. Abbreviations: ABA (abscisic acid), CPK (calcium-dependent protein kinase), MAPK (mitogen-activated protein kinase), ABF (ABA-responsive element binding factor), ERF (ethylene-responsive element binding factor), HSF (heat shock transcription factor), WRKY (WRKY transcription factors), ABRE (ABA-responsive element), ERE (ethylene-responsive element).

DETAILED DESCRIPTION OF THE INVENTION

Higher plants exhibit a remarkable phenotypic plasticity to adapt to adverse environmental changes. The Greater Duckweed *Spirodela*, as an aquatic plant, presents exceptional tolerance to cold winters through its dormant structure of turions in place of seeds. Abundant starch in turions permits them to sink and escape the freezing surface of waters. Due to their clonal propagation, they are the fastest growing biomass on earth, providing an as yet an untapped source for industrial applications.

We used next generation sequencing technology to examine the transcriptome of turion development triggered by exogenous ABA. A total of 208 genes showed more than a 4-fold increase compared with 154 down-regulated genes in developing turions. The analysis of up-regulated differential expressed genes in response to dormancy exposed an enriched interplay among various pathways: signal transduction, seed dehydration, carbohydrate and secondary metabolism, and senescence. On the other side, the genes responsible for rapid growth and biomass accumulation through DNA assembly, protein synthesis and carbon fixation are repressed. Noticeably, three members of late embryogenesis abundant protein family are exclusively expressed during turion formation. High expression level of key genes in starch synthesis are APS1, APL3 and GBSSI, which could artificially be reduced for re-directing carbon flow from photosynthesis to create a higher energy biomass.

The identification and functional annotation of differentially expressed genes opens a major step towards understanding the molecular network underlying vegetative frond dormancy. Moreover, genes have been identified that could be engineered in duckweeds for practical applications easing agricultural production of food crops.

In another aspect of the invention we have investigated the unusual mechanism of the regulation of organellar gene expression where the translation of organellar RNAs requires the replacement of a C with a U before translation, also referred to as RNA editing. Sequence specificity is achieved through a nuclear gene family that encodes PLS-type pentatricopeptide repeat proteins (PPRs). Within monocotelydonous plants, most genomes that have been sequenced belong to the order of Commelinids, but sequencing of species of the *Alismatales*, *Spirodela* (*Spirodela polyrhiza*), has providing us with a new reference for the evolution of PPR proteins, and means to modulate expression of the same to confer desirable phenotypes. We used deep sequencing of non-ribosomal total RNA to determine the number and conversion efficiency of editing sites of *Spirodela* organellar mRNA. There are 66 editing sites, of which 58 are in protein coding regions. Comparison to coconut, maize, and rice suggests that RNA editing originated from a common ancestor, but that the number of PPR genes and editing sites changed independently either by losses or gains of gene copies during evolution. Based on the expression of nuclear-encoded PPR genes and RNA editing efficiency in plastids, it appears that for ~24% of incomplete RNA editing is the result of lower level expression of individual PPR genes. Furthermore, 37 PPR genes are differentially expressed and 11 RNA editing sites show a significant change when growth is arrested at dormancy. Thus, it appears that RNA editing is regulated through the expression of gene copies in a developmental fashion.

Definitions

The term "duckweed system" or "duckweed culture" as used herein encompasses duckweed plant cultures, duckweed fronds or immature turion cultures, duckweed suspension cultures, and duckweed protoplast cell cultures.

The term "duckweed plant culture" as used herein refers to a culture comprising mostly fully differentiated duckweed plants.

A "differentiated cell," as used herein, is a cell having at least one phenotypic characteristic (e.g., a distinctive cell morphology or the expression of a marker nucleic acid or protein) that distinguishes it from undifferentiated cells or from cells found in other tissue types. In some embodiments, the duckweed turion culture comprises duckweed turions as described elsewhere herein.

The term "duckweed suspension culture" as used herein refers to a culture comprising dispersed duckweed cells, for example dispersed duckweed callus cells. Generally, a duckweed suspension culture will comprise both single cells and unorganized cellular aggregates of varying sizes.

The term "duckweed protoplast cell culture" refers to a culture comprising duckweed cells where at least about 50%, 60%, 70%, 80% or 90% of the duckweed cells lack a cell wall. Methods for making protoplast cells from plant cells are described, for example, in Eriksson (1995) in Plant Protoplasts, Fowke et al., eds., CRC Press, herein incorporated by reference.

The term "biological function" as used herein refers to a biological activity or property of a nucleic acid molecule or polypeptide. For example, biological functions for nucleic acid molecules include modulating biological responses, coding for polypeptides, and modulating the expression of target nucleotide sequences. Examples of biological functions for polypeptides include modulating biological responses, conferring structural properties of interest, conferring biochemical activities of interest, and conferring regulatory activities of interest. Particular, non-limiting examples of modulatory and regulatory activities include the ability to bind a substrate of interest, the ability to bind a ligand of interest, the ability to catalyze a reaction of interest, the ability to modulate a response to a plant hormone, the ability to modulate a response to a plant growth regulator, the ability to modulate a response to environmental perturbation, the ability to modulate a response to physiological perturbation, the ability to modulate a response to one or more pathogens, and the ability to modulate a response to one or more toxins.

The term "duckweed" refers to members of the family Lemnaceae. This family currently is divided into four genera and 34 species of duckweed as follows: genus *Spirodela* (*S. polyrrhiza, S. intermedia, S. punctata*); genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wolfiella* (*Wl. caudata, Wl. denticulata, Wl. gladiata, Wl. hyalina, Wl. lingulata, Wl. repunda, Wl. rotunda, and Wl. neotropica*). Any other genera or species of Lemnaceae, if they exist, are also aspects of the present invention. *Lemna* species can be classified using the taxonomic scheme described by Landolt (1986) Biosystematic Investigation on the Family of Duckweeds: The family of Lemnaceae—A Monograph Study Geobatanischen Institut ETH, Stiftung Rubel, Zurich.

"Operably linked" as used herein in reference to nucleotide sequences refers to multiple nucleotide sequences that are placed in a functional relationship with each other. For example a promoter nucleotide sequence is operably linked to a second nucleotide sequence when it is positioned such that it can drive the transcription of the second nucleotide sequence.

"Polypeptide" refers to any monomeric or multimeric protein or peptide.

"Biologically active polypeptide" refers to a polypeptide that has the capability of performing one or more biological functions or a set of activities normally attributed to the polypeptide in a biological context. Those skilled in the art will appreciate that the term "biologically active" includes polypeptides in which the biological activity is altered as compared with the native protein (e.g., suppressed or enhanced), as long as the protein has sufficient activity to be of interest for use in industrial or chemical processes or as a therapeutic, vaccine, or diagnostics reagent. Biological activity can be determined by any method available in the art. For example, the biological activity of members of the interferon family of proteins can be determined by any of a number of methods including their interaction with interferon-specific antibodies, their ability to increase resistance to viral infection, or their ability to modulate the transcription of interferon-regulated gene targets.

"Nucleotide sequence of interest" as used herein refers to any nucleotide sequence encoding a polypeptide intended for expression in duckweed. For example, nucleotide sequences encoding therapeutic (e.g., for veterinary or medical uses) or immunogenic (e.g., for vaccination) polypeptides can be expressed using transformed duckweed according to the present invention.

The terms "expression" or "production" refer to the biosynthesis of a gene product, including the transcription, translation, and assembly of said gene product.

The term "genetically modified" as used herein refers to a plant cell or plant that is modified in its genetic information by the introduction of one or more foreign polynucleotides, and that the expression of the foreign polynucleotides leads to a phenotypic change in the plant. For example, a plant that is genetically modified to alter glycosylation is modified in its genetic information by the introduction of one or more foreign polynucleotides, where expression of the polynucleotide or polynucleotides leads to a change in glycosylation in the plant.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim, an in the latter instance, impurities ordinarily associated with the specified material(s). The term "consisting essentially of" limits the scope of a claim to the specified elements, steps or materials and those that do not materially affect the basic and novel characteristic(s) of the claimed subject matter.

The following methods are provided to facilitate the practice of the present invention.

Sample Preparation

*Spirodela polyrhiza* 7498 was grown into half-strength Schenk and Hildebrandt basal salt mixture (Sigma, S6765) with 1% sucrose liquid medium under 6-hrs light, 8-hrs dark photoperiod. Plant tissues from four biological replicates for fronds without ABA treatment and developing turions with 3-day 10 µM ABA were collected and frozen in liquid nitrogen. 10 µg of total RNA was extracted for each sample by RNA-easy Qiagen kit with RLC buffer due to second metabolites. Ribosomal RNA was depleted with a kit from Epicenter (MRZPL116) in order to increase the coverage of other RNA classes. Vegetative fronds and turions with 14 days ABA treatment were fixed, embedded, and examined under transmission electron microscope as described[13, 20].

Library Construction and Sequence Quality Control

We started with ~300 ngrRNA-depleted total RNA, fragmented the RNA, performed reverse transcription and size-selected the cDNA, used Emulsion PCR to amplify the complex gene libraries and prevent formation of chimeric cDNA products. All steps followed the manufacturer's guide (SOLiD™ total RNA-Seq kit). To minimize potential experimental batch effect, eight samples were barcoded, pooled, and evenly distributed into three lanes. The single-end reads with the size of 75 bp were generated with our in-house SOLiD 5500 platform. The Exact Call Chemistry (ECC) module was utilized in the sequencing run, which is an optional kit that is used to further enhance sequencing accuracy by generating reference-free bases directly. After quality trimming with score of 20, reads with a minimum length of 40 bp were saved.

Read Mapping and Quantifying Gene Expression

The remaining reads were mapped to the reference genome *Spirodela polyrhiza* 7498 (GenBank Accession #ATDW01000000), which was recently sequenced, assembled, and annotated, by using TopHat 2[21] with Bowtie[22]. TopHat is a fast splice junction mapper for RNA-Seq reads. It aligns RNA-Seq reads to reference genomes using the ultra high-throughput short read aligner Bowtie, and then analyzes the mapping results to identify splice junctions between exons. Gene expression levels were normalized using fragments per kilobase of exon per million mapped reads (FPKM). Transcript abundance and deferential gene expression were calculated with Cufflinks[23]. DE genes were defined, as when their absolute value of log 2 fold change was higher than 2 and their P value was less than 0.01.

As a positive control for our measurements, we used independent data obtained in a separate study under the same induction conditions as in this study from the expression of ADP-glucose pyrophosphorylase genes with qRT-PCR [13]. As a negative control, we used northern blot data of the expression of the tur4 gene obtained in yet another study [24].

Functional Annotation and Cis-Element Predictions

For each DE gene, GO annotation was obtained with the program of blast2go, which uses a blast algorithm to assign GO terms to sequences based on similarity[25]. GO enrichment was performed in two groups of gene sets, respectively, one of highly expressed transcripts in turions, the other one of highly expressed transcripts in fronds based on the whole gene set of the *Spirodela* genome using GOseq, which adjusts the bias from gene lengths[26]. The cis-acting regulatory DNA elements were predicted by signal scan search from PLACE database[27]. PLACE is a database of motifs found in plant cis-acting regulatory DNA elements, all from previously published reports. We dissected 1-kb regions upstream of DE genes and scanned them for potential pairs of TFs and cis-elements.

The following example is provided to illustrate certain embodiments of the invention. It is not intended to limit the invention in any way.

Example I

To further uncover the regulation of gene expression as the phase switches, we took advantage of RNA deep sequencing, and compared the transcriptome between fronds and developing turions. A more comprehensive understanding of the gene repertoire and its regulation during turion formation has great potential for industrial applications including the redirection of carbon flow into higher energy products.

Calibration and Selection of Tissue Samples

A comprehensive study for turion formation has been done using abscisic acid (ABA) induction[14, 15, 17, 28, 29]. Three days after ABA induction, the *Spirodela* primordium is committed to turion development, which cannot be reversed. All primary biosynthesis of protein, mRNA and DNA are shutdown resulting in the onset of the dormant state[28]. To calibrate our growing conditions with previous investigations, we used transmission electron microscopy (TEM) to investigate different developmental stages. We chose fronds and developing turions with 3 days after ABA treatment instead of 14 days because 14-day treatment is not a key transition state and RNA purification is greatly hampered by high content of starch, but mature turions with 14-days treatment provide a more complete structural image through TEM. Turion cells have thicker cell walls, multiple smaller vacuoles and distorted plastids filled with abundant starch granules, whereas frond cells differ with having well-shaped chloroplasts consistent with previous observations (FIG. 1). Therefore, growing conditions and turion induction appear to be reproducible.

Mapping RNA-Seq Reads

We used eight samples in total, with each condition having four biological replicates. To eliminate potentially technical variation from biological replicates, they were multiplexed, pooled, and sequenced with the SOLiD 5500 platform. A total of 15~41 million quality reads per sample were generated after filtering raw reads (Table 1).

The high quality reads were mapped to chloroplast[30], mitochondria[31], and nuclear genomes[32], respectively. We could clearly divide sequence reads into these three classes. Surprisingly, there was an abundance of organelle-derived transcripts with 28~39% of total reads. With this depth of data we could assemble sequences for complete plastid and mitochondrial transcriptomes. The high proportion of organelle reads stresses the important roles of their transcripts, provides us with their expression profiles and facilitates the phylogenetic analysis[33]. Based on the combined reads of nuclear and organelle RNAs, more than 89% of our RNA-Seq reads were mappable, attesting to the performance of the sequencing platform. It also suggests that part of previously unmapped reads in other studies remained undetected because of their organellar origin[5, 34-36]. We still found that 1~9% of total reads were derived from ribosomal RNA, which is an indication that the protocol for the depletion of ribosomal RNA from samples was reasonably successful. Such efficiency is critical for mainly uncovering the desired transcriptome with complete coverage and in a cost-effective manner[37].

Among the total reads, 53-61% originated from nuclear DNA, lower than in other cases with about 80% of mappable sequences [34, 36]. The reason could be the method we used through ribosomal RNA removal rather than polyA selection. In case of polyA selection, organelle transcripts are automatically removed due to the lack of the polyA tail in organelle transcripts, whereas most of them were captured by our method of ribosomal RNA removal. Excluding the abundant organelle and rDNA reads, nuclear reads corresponded to 29~72X coverage for all annotated genes (Table 1), demonstrating that the depth used in our study was sufficient to cover the *Spirodela* nuclear transcriptome.

Identification and Validation of Differentially Expressed Genes

Comparison of frond and developing turion samples provided us with 362 differentially expressed (DE) genes. A total of 117 had greater than 10-fold difference in mRNA levels and 208 genes were up-regulated and expressed at higher levels in developing turions than in fronds, whereas 154 genes were down-regulated, indicating lower expression in turions than in fronds (Table 2).

Figure 2:
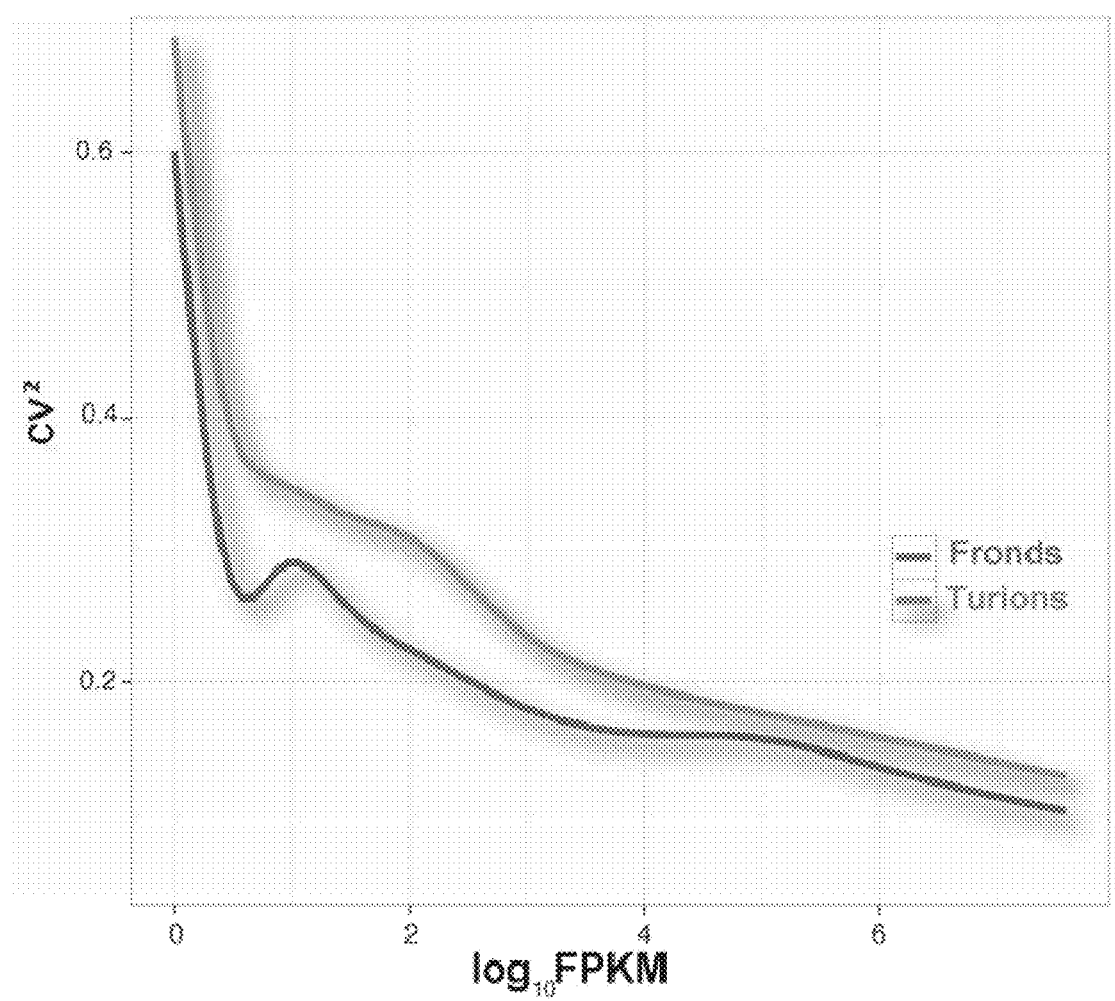
FIG. 2. Biological variation for biological replicates from fronds and developing turions. Biological variation was represented by the square coefficient of variation of FPKM values for each gene ($CV^2$).

Previous studies had indicated that a small number of biological replicates might not be robust enough because it is impossible to know whether expression patterns are specific to individuals or are characteristic for the total population. Even for RNA deep sequencing, a sufficient number of biological replicates are still required to have confidence in the measurements[38-40]. Because two biological replicates usually are not sufficient to account for sample variability, we increased this number to four independent biological replicates. The coefficient of variation to the power of two ($CV^2$), a normalized measure of crossreplicate variability that can be useful for evaluating the quality of RNA-Seq data, was calculated to exhibit the biological variation (FIG. 2). As expected, the data showed that the abundance of the genes varied between replicate RNA samples, especially for ones with lower FPKM values. However, with four biological replicates, which take variation within the target population into account and also counteract random technical variation[23, 41], we were very confident to assess gene expression levels with accuracy.

Figure 3:
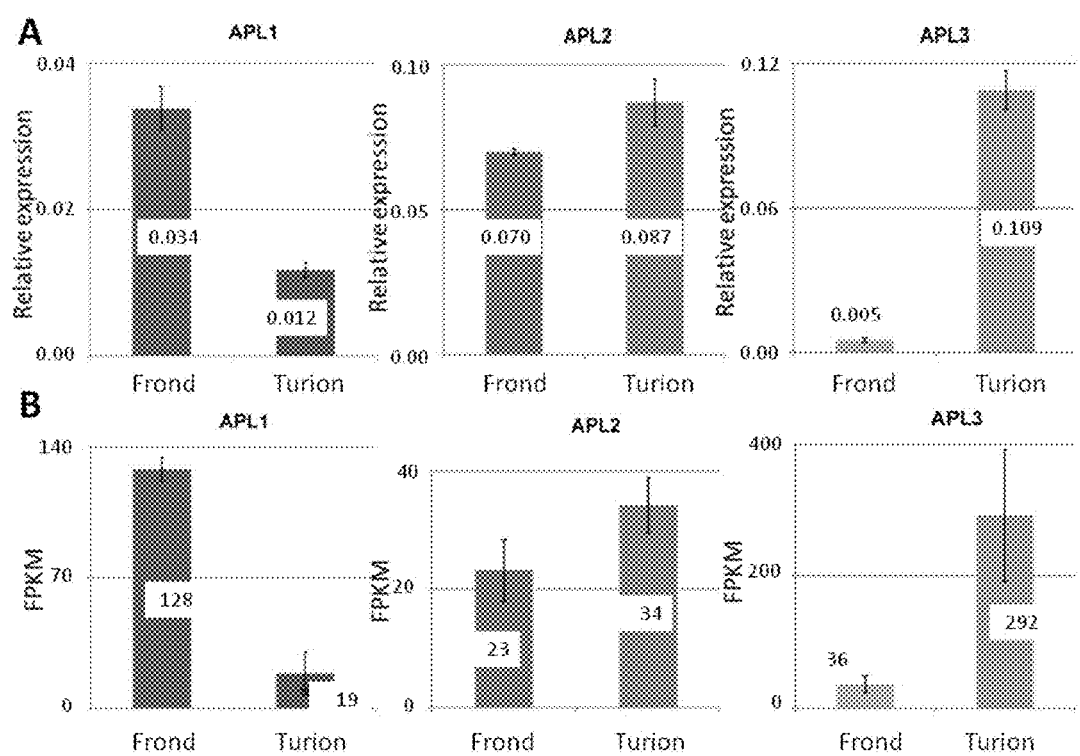
FIG. 3. Comparison of APL gene expression from qRT-PCR vs. RNA-Seq. A. APL gene expression from qRT-PCR.

As another quality control, we could rely on our measurements of the 3 transcripts of ADP-glucose pyrophosphorylases (APLs) for starch synthesis[13], which were done with qRT-PCR, and compared with the RNA-Seq data. Indeed, the correlation co-efficient of 0.992 indicated that the two independent measurements were consistent and showed similar patterns: APL1 (GenBank Accession #JN180634) was highly expressed in fronds and APL3 (GenBank Accession #JN180636) showed the most abundance in developing turions. However, APL2 (GenBank Accession #JN180635) was not identified as DE gene due to only 1.5 times of difference at the time point of 0 and $3^{rd}$ day by the threshold value of 4 (FIG. 3). A fourth gene, tur4, provided us with a negative control from an independent study [24]. The tur4 gene has the Gene ID Spipo7G0013500 in the sequenced genome of Spirodela. Expression of this gene during turion formation was studied with Northern blot analysis. Although the tur4 gene responded to ABA treatment within hours, it appeared to return to nearly normal levels of expression thereafter. Northern blot analysis showed no induction at day 3 after ABA treatment, whereas we could still detect a 2-fold increase in tur4 expression with RNA-Seq, indicating that our method is more sensitive than Northern blot analysis. However, given both the APLs and tur4 results, we selected a cut-off for DE genes at 4-fold expressional change.

Response to ABA Stimulus

The plant hormone abscisic acid (ABA) plays a major role as a signal in seed development and plant dormancy[42, 43] and regulates many important aspects, such as the synthesis of seed storage proteins, starch and lipids[44, 45]. In Spirodela, exogenous ABA effectively triggers entry into the dormant state (turions) from growth phase (fronds)[15]. We found 25 up-regulated DE genes in response to ABA stimulus or regulation based on their GO annotation (Table 3 and S1). The pathway of ABA signal transduction and response seemed to be interwoven with enzyme metabolism (kinase, synthase, and phosphatase) and other signaling pathways (transporter, ethylene). Northern blot analysis shows that ABA rapidly up-regulates tur4 transcriptional level that encodes a peroxidase, which could stimulate turion formation and growth inhibition[24].

Growth Inhibition

Dormancy is generally defined by the lack of visible growth. The shoot apices cease active growth in perennial plants when a state of dormancy is reached. The seed dormancy is observed in seeds with a quiescent phase preventing germination. The same phenomenon was investigated for Spirodela in the presence and absence of growth. When we looked at DE genes associated with Spirodela growth by RNA-Seqdata, we found genes of histone H3 (Spipo9G0039400, Spipo0G0046100 and Spipo13G0007500) and H4 (Spipo28G0019000), ribosomal protein (Spipo1G0126300), expansins (Spipo22G0026300), aquaporins (Spipo11G0033800, Spipo17G0045100), ribulose-1,5-bisphosphate carboxylase oxygenases (RuBisCO) (Spipo19G0027700, Spipo23G0013400) for carbon fixation were down-regulated in turions (Table 4). In eukaryotic cells, DNA replication requires the synthesis of histone proteins to package newly replicated DNA into nucleosomes. Expansins are a key endogenous regulator of plant cell enlargement[46]. Aquaporins support cell growth and especially contributes to cell expansion and cell division. The gene that is highly expressed in fronds (69 times higher than in turions) is aquaporin (Spipo11G0033800) (Table 4). Over-expression of aquaporin stimulates cell growth in tobacco[47] or in Arabidopsis[48]. These results further confirm our knowledge that fronds are mainly responsible for rapid growth through actively DNA assembly, protein synthesis and carbon fixation, leading to a quick biomass increase, in comparison to the turions, where these processes are greatly decreased. Previous studies also suggested this mechanism of the turion formation by measuring DNA, RNA and protein content, which showed that DNA, protein and RNA biosynthesis were largely inhibited, resulting in the decrease of cell division, expansion and differentiation [28].

Late Embryogenesis Abundant Protein (LEA) Genes are a Valuable Marker for Dormancy On the other hand, we found some specific mRNAs were increased in developing turions, for example LEAs. Although there were five members of LEA genes (Spipo14G0001200, Spipo5G0015500, Spipo0G0166800, Spipo1G0033500, Spipo26G0007700) with increased expression in turions, the LEA gene (Spipo0G0166800) was the most up-regulated DE gene, two other LEA genes (Spipo5G0015500 and Spipo14G0001200) were exclusively expressed in developing turions (Table 5). Indeed, the promoter of these LEA genes would be ideal to ensure expression of other coding regions exclusively in turions through transgenic approaches. Additionally, LEA was found to protect other proteins against desiccation, cold, and high salinity[49] and especially accumulates when plant seeds desiccate[50]. Given their high induction, they provide valuable markers for dormancy in general. In response to dehydration, endogenous ABA levels increased dramatically followed by induction of LEA[51]. As expected, when Spirodela fronds are destined to dormant turions triggered by ABA, desiccation is an indispensable step, in which LEA proteins play pivotal roles to preserve the cellular structures and nutrients in turions.

Genes Involved in Carbon Partitioning

Starch is the major carbon reserve in plant storage organs, and ABA has a signaling role by inducing starch biosynthetic gene expression and co-ordinate carbohydrate partitioning[52]. In our study, four genes (Spipo12G0062400, Spipo18G0038500, Spipo16G0027000 and Spipo27G0011300) (Table S1) participating in starch biosynthesis were significantly enhanced in developing turions. The qRT-PCR experiment confirmed the key enzyme of large-subunit ADP-glucose pyrophosphorylase 3 (APL3) for starch biosynthesis was highly expressed in turion development[13]. The RNA-Seq study for Landoltia punctata also revealed gene expression involved in starch biosynthesis was up-regulated under nutrient starvation[53]. Another way to accumulate starch content is to redirect carbon flow to starch biosynthesis. We found seven genes participate in the degradation of lipids by alpha- (Spipo0G0156600, Spipo0G0180000, Spipo0G0156500, Spipo5G0040500) or beta-oxidation (Spipo0G0179100, Spipo3G0031300, Spipo1G0110400), which probably allocate carbon to starch rather than fatty acids to achieve denser turions that sink to the bottom of streams during seasons (Table S1). Previously, it has been shown that the carbon flow into seeds can be rebalanced between different macromolecules with different energy content [54]. Reallocation of carbon is critical for the improvement of oil production in novel crops in the future. In oilseed species, numerous biotechnological approaches have been carried out that were aimed to maximize the flow of carbon into oil by over-expression of enzymes of the TAG assembling network[55]. Although one might argue that turions would no longer be able to sink in water when filled with lipids, in those applications biomass would be accumulated under constant temperature.

Another way to investigate the balance of carbon partitioning can be derived from the average FPKM value (Fragments Per Kilobase of transcript per Million mapped reads) of all the key genes encoding both pathways. The genes encoding for lipid production were expressed relatively low with FPKM of 28 and 22 in fronds and turions, respectively. Therefore, the level of lipids remains low throughout development (Table S2). Given the high level of starch in turions, genes in lipid production are not induced, whereas the ones for starch biosynthesis are during turion formation, providing us with a correlation between metabolic products and the regulation of the corresponding pathways. Given this correlation, we hypothesize that we could redirect carbon flow into lipids by blocking key genes of such as AGPS1, AGPL3, GBSSI and ACCase4, GPAT1, DGAT2, and over-express transcripts of the lipid pathway (Table S2) together with turion-specific promoters, like LEAs (Spipo14G0001200, Spipo5G0015500, Spipo0G0166800)(Table 5).

Turion-Specific Pathways

We found that the transcriptome also closely links the turion phenotypic variation with thick cell wall and abundant secondary metabolites like pigment. The expressions of eight members of the UDP-glycosyltransferase superfamily (Spipo2G0010600, Spipo2G0043800, Spipo16G0044000, Spipo2G0039000, Spipo14G0034300, Spipo2G0124000, Spipo5G0014300, Spipo2G0077900) and two of the cellulose synthases (Spipo28G0017100, Spipo7G0044000) involved in cell wall biosynthesis were increased (Table S1). Three dihydro flavonol reductases (Spipo7G0010700, Spipo10G0000200, Spipo14G0054900) and one flavonoid 3',5'-hydroxylase (Spipo0G0155000) involved in the anthocyanin pathway were up-regulated (Table S1). In addition, we found the average FPKM value for all key enzymes of lignin biosynthesis were 23 in fronds but 41 in turions, which may explain the rigidity of cell wall in turion cells to defend water pressure at the bottom of waters (Table S2).

To gain a broad overview into the biological functions for DE genes, we next performed an analysis of gene ontology (GO) enrichment (Methods). We found a total of 24 enriched pathways (p<0.01) in developing turions, whereas no enriched GO was found in fronds under the null hypothesis of the entire gene set of *Spirodela* (Young et al., 2010). The clustered DE genes were mainly related to response to ABA, fatty acid oxidation, and ion transportation. The GO functions of leaf senescence and cell wall modification were also highlighted (Table 6).

Transcriptional Regulation of Differentially Expressed Genes

Transcription factors (TFs) are crucial components of regulatory systems, which initiate vital changes in gene expression. Thus, we examined TF gene models and found nine TFs were significantly changed including two ABA-responsive element binding factors (bZIP, Spipo4G0008600 and Spipo2G0055800), four Ethylene-responsive element binding factors (ERFs, Spipo0G0155100, Spipo3G0031800, Spipo20G0027700 and Spipo11G0028200), two heat shock TFs (HSFs, Spipo8G0037600 and Spipo9G0002000), and one WRKY TF (Spipo8G0045500) (Table 5 and S1).

ABA-Responsive Element Binding Factor

The bZIP transcription factors regulate plant development through a basic region and a leucine zipper dimerization motif that binds to DNA[56, 57]. In the complete sequence of *Spirodela* genome[32], an exhaustive search of the bZIP superfamily was performed and 41 members identified. Among them, seven genes belong to the ABA-responsive element binding factors (ABFs), i.e., the bZIP superfamily group A due to their structural features with conserved regions C1-C2, basic regions, and leucine zippers (FIG. 4)[56, 58]. This group is thought to play a central role in controlling ABA-responsive gene expression in seeds and vegetative tissues via binding to ABA-responsive-elements (ABREs). For example, ABI5, one member of ABFs, induces LEA expression by binding to its promoters during seed maturation[58]. Here, all seven genes showed differentially increased expression levels, whereas only SpABF1 (Spipo4G0008600) was defined as a DE gene due to a significant change (Table 5). Noticeably, SpbZIP (Spipo2G0055800), another bZIP transcription factor, was significantly decreased in developing turions (Table 5). It shared leucine residues in the basic domain but missing other 2 conserved regions, corresponding to bZIP group I in *Arabidopsis*. Studies of group I genes from several species indicate that they might play a role in vascular development [56]. SpbZIP might positively regulate xylem and phloem development, too. Because both structure and function of turions are equivalent to seeds, less vascular tissue is needed in turions compared to fronds and the expression of SpbZIP is decreased accordingly. Thus, we conclude that a specific subset of bZIP transcription factors are involved in turion formation.

Other TFs Involved in ABA-Mediated Gene Expression

In addition to ABF TFs, other TFs were also identified to be involved in turion development. Ethylene-responsive element binding factors (ERFs) are transcription factors that are specific to plants. A highly conserved DNA binding domain, known as the ERF domain interacting directly with the GCC box in the ethylene-responsive-element (ERE), is the unique feature of this protein family[59] (FIG. 5). ERFs also play a role in a variety of developmental processes such as flower, seed development[60], and fruit ripening[61]. We identified 57 ERF genes in the *Spirodela* genome, where SpERF1 (Spipo0G0155100), SpERF2 (Spipo3G0031800), and SpERF3 (Spipo20G0027700) were significantly up-regulated and SpERF4 (Spipo11G0028200) down-regulated in response to turion development (Table 5). It had been reported that AtERF1, AtERF2, ATERF5 functioned as activators of GCC box-dependent transcription in *Arabidopsis* leaves, but AtERF3 and AtERF4 acted as repressors[57, 59]. It also was shown that ERF2 and ERF4 enhanced the transcription of a reporter gene in tobacco protoplasts[62]. The three highly up-regulated ERFs in *Spirodela* turions should therefore play an important role in turion development.

Heat shock transcription factors (HSFs) are transcriptional activators of heat shock genes. An increasing number of studies indicated that some HSFs appeared during the maturation stage of the seed, when cell division ceased and seeds adapted to desiccation and long-term survival[63]. Here, the increased expression of two HSFs (Spipo9G0002000 and Spipo8G0037600) (Table 5) might also indicate an important function for turion desiccation and survival during long periods of winter.

WRKY transcription factors (TFs) are key regulators of many plant processes, including the responses to biotic and abiotic stresses, senescence, seed dormancy, and seed germination[64]. In vivo and in vitro promoter-binding studies showed that WRKY TFs could either activate or repress the expression of downstream ABFs through W-box sequences present in their promoters[65]. However, whether the *Spirodela* WRKY TF (Spipo8G0045500) (Table 5) is a repressor or activator needs to be further investigated.

Together, the significant changes in the expressions of ABFs, ERFs, HSF and WRKY TF reflected their obligatory regulation during turion development. Their involvement in the transition from fronds to turions and their control of spatial and temporal expression of target genes provides us also with new tools to create specialized traits through tailoring of chimeric genes.

Cis-Element

Control of gene expression is achieved through the binding of transcription factors to specific cis-elements in promoter regions of target genes[66]. To predict potential pairs of TFs and cis-elements, we scanned a 1-kb region upstream of DE genes with the PLACE database[27]. We found 30 up-regulated DE genes containing the cis-element of ABA-responsive element (ABRE: YACGTGGC) and 119 with ethylene-responsive element (ERE: GCCGCC) (Table S1). These target genes of ABFs and ERFs are associated with seed dehydration (like late embryogenesis abundant proteins), regulatory transcription factor, protein kinases and phosphatases (like CPK, MAPK), carbohydrate and secondary metabolism (like cellulose synthase and stachyose synthase), and senescence-associated proteins (like Glutathione-S-transferase).

Discussion

ABA is essential for seed maturation and also enforces a period of seed dormancy so that the seeds do not germinate prematurely during unseasonably conditions. The same behavior is seen in dormant *Spirodela* turions that are induced by low temperature, limited nutrition, or exogenous ABA[67]. The external stimuli rapidly induce both $Ca^{2+}$ influx and endogenous ABA synthesis[68]. In maturing seed, ABA-regulated genes include those required for the synthesis of storage reserves and the acquisition of desiccation tolerance. $Ca^{2+}$ can act as secondary messenger to activate the expression of cascade components of calcium-dependent protein kinase (CPK) and mitogen-activated protein kinase (MAPK). The structure of CPK shows there are four $Ca^{2+}$-binding EF hand domains allowing the protein to function as a $Ca^{2+}$ sensor. In addition to $Ca^{2+}$, reversible phosphorylation also regulates kinase activity[69]. A number of studies have demonstrated that MAPKs in *Arabidopsis* are associated with hormone biosynthesis and signaling including ethylene and ABA[43]. Both of CPK and MAPK could phosphorylate a wide range of target proteins, including other kinases and/or transcription factors[44, 57], in particular SpERF of Spipo0G0155100, Spipo3G0031800 and Spipo20G0027700, SpABF of Spipo4G0008600 and Spipo2G0055800, SpHSF of Spipo8G0037600 and Spipo9G0002000, and SpWRKY of Spipo8G0045500 (Table 5). The activation of TFs ultimately regulates their target genes to cease cell division but begin to accumulate secondary metabolites. As shown in flowering seeds, aspects of reserve accumulation and late embryogenesis abundant (LEA) gene expression are controlled largely by the coordinated action of transcription factors[44]. Taken together, we generated a model summarizing the signal transduction leading to *Spirodela* dormancy based on integration of our result and previous knowledge (FIG. 6).

CONCLUSIONS

Many studies have been concerned with seed development in plants. Seeds are the product of sexual reproduction and the segregation of Mendelian traits. They also represent a dormant state in the life cycle of the plant and they compartmentalize nutrients for growth in the absence of photosynthesis. Agriculture could not exist without these properties of plants. Here, we studied a plant that propagates by clonal division and can undergo dormancy without forming seeds. The aquatic plant *Spirodela* could not survive on water surface without human intervention, when the water freezes. It simply switches to dormancy and accumulates starch that allows it to sink to the bottom of the water to escape the ice. Besides low temperature, however, the same switch can be achieved with the hormone ABA that has been shown to perform the same change for seed maturation. Using such an induction with *Spirodela*, we can study genes that regulate dormancy. Here, we isolated total RNA exclude ribosomal RNA before and at the onset of dormancy, sequenced them with next-generation technology, and identified the transcripts by mapping them back to the genome sequence. The detailed analysis of the transcriptional landscape of differentially expressed genes provides the first comprehensive view at the dormancy of aquatic plants. On the other hand, research studies have been initiated with the goal of developing duckweed species as an alternative to algae for oil production with the fact of fast growth and quick biomass accumulation[70]. The expression data for lipid and starch biosynthesis together with the turion-specific transcriptional genes from our RNA-Seq data would be the ideal targets to develop duckweeds into oil crops.

TABLE 1

Summary of sequence read alignments to three genome references.

| Sample | Qualified total reads | Reads # map nuclear genome | Map nuclear genome | Nuclear coverage | Map chloroplast | Map mitochondria | Map rDNA |
| --- | --- | --- | --- | --- | --- | --- | --- |
| fronds 1 | 24,356,014 | 12,795,916 | 53% | 42 | 35% | 1% | 4% |
| fronds 2 | 41,310,111 | 22,039,845 | 53% | 72 | 37% | 3% | 4% |
| fronds 3 | 28,333,911 | 16,444,539 | 58% | 54 | 29% | 2% | 6% |
| fronds 4 | 28,188,669 | 16,282,775 | 58% | 53 | 30% | 2% | 9% |
| turions 1 | 26,484,522 | 15,431,023 | 58% | 50 | 28% | 2% | 1% |
| turions 2 | 28,466,211 | 16,123,639 | 57% | 53 | 34% | 2% | 2% |
| turions 3 | 25,754,050 | 15,697,393 | 61% | 51 | 26% | 2% | 3% |
| turions 4 | 14,996,833 | 8,824,987 | 59% | 29 | 29% | 2% | 1% |

TABLE 2

Fold change in differentially expressed genes between in fronds and developing turions at FDR <0.01.

| | Fold change | | | | | |
| --- | --- | --- | --- | --- | --- | --- |
| | 4.0-5.0 | 5.1-10 | 10.1-15 | 15.1-20 | >20 | Sum |
| Genes expressed lower in turions than fronds | 37 | 73 | 12 | 10 | 22 | 154 |
| Genes expressed higher in turions than fronds | 38 | 97 | 25 | 15 | 33 | 208 |

TABLE 3

FPKM for Up-regulated DE genes in response to ABA stimulus.

| Gene ID | Fold change | Frond FPKM | Turion FPKM | Annotation |
|---|---|---|---|---|
| Spipo6G0001100 | 146 | 0.3 | 45.3 | Peripheral-type benzodiazepine receptor |
| Spipo5G0029200 | 57 | 0.8 | 48.1 | Major facilitator superfamily protein |
| Spipo19G0014500 | 43 | 0.5 | 22.4 | Galactinol synthase |
| Spipo26G0007700 | 17 | 8.4 | 140.0 | Late embryogenesis abundant protein LEA |
| Spipo8G0058900 | 16 | 1.2 | 19.4 | Flowering locus T/Terminal flower 1-like protein |
| Spipo4G0016300 | 15 | 15.2 | 235.2 | Annexin |
| Spipo18G0029800 | 15 | 28.7 | 420.3 | O-acetyltransferase-like |
| Spipo3G0078900 | 14 | 0.4 | 6.2 | Stachyose synthase, putative |
| Spipo0G0155100 | 13 | 1.7 | 21.5 | Ethylene-responsive transcription factor 1 |
| Spipo0G0130700 | 9 | 1.6 | 15.5 | C4-dicarboxylate transporter |
| Spipo7G0041900 | 7 | 1.4 | 9.8 | ABC transporter G family member |
| Spipo3G0031800 | 7 | 10.3 | 74.2 | Ethylene-responsive transcription factor 2 |
| Spipo8G0062500 | 6 | 7.2 | 44.3 | Receptor-like protein kinase |
| Spipo14G0026800 | 5 | 4.0 | 18.3 | Eukaryotic aspartyl protease family protein |
| Spipo12G0003900 | 4 | 37.9 | 162.9 | myb domain protein 73 |
| Spipo5G0040500 | 8 | 23.1 | 189.7 | Alpha-dioxygenase |
| Spipo0G0156500 | 6 | 15.5 | 97.9 | Alpha-dioxygenase |
| Spipo0G0180000 | 6 | 98.0 | 561.3 | Alpha-dioxygenase |
| Spipo0G0156600 | 5 | 19.5 | 104.4 | Prostaglandin G/H synthase |
| Spipo8G0046200 | 67 | 0.2 | 15.6 | Protein phosphatase 2c, putative |
| Spipo3G0013100 | 38 | 0.5 | 20.2 | NAC domain-containing protein 67 |
| Spipo23G0012800 | 32 | 1.1 | 34.2 | Protein phosphatase 2C |
| Spipo21G0022300 | 10 | 6.1 | 59.1 | Protein phosphatase 2c, putative |
| Spipo1G0021700 | 6 | 3.2 | 18.9 | Protein phosphatase 2c, putative |
| Spipo6G0056800 | 4 | 11.5 | 46.5 | NAC domain-containing protein 67 |

TABLE 4

FPKM for Down-regulated DE genes associated with Spirodela growth.

| Gene ID | Fold change | Frond FPKM | Turion FPKM | Annotation |
|---|---|---|---|---|
| Spipo11G0033800 | 69 | 33.6 | 0.5 | Aquaporin |
| Spipo17G0045100 | 5 | 86.3 | 17.8 | Aquaporin |
| Spipo22G0025300 | 5 | 186.4 | 40.4 | Expansin |
| Spipo9G0039400 | 7 | 68.2 | 9.4 | Histone H3 |
| Spipo0G0046100 | 7 | 112.4 | 16.4 | Histone H3 |
| Spipo13G0007500 | 6 | 159.5 | 27.5 | Histone H3 |
| Spipo28G0019000 | 5 | 77.9 | 14.8 | Histone H4 |
| Spipo3G0024800 | 14 | 1018.4 | 71.2 | Pre-rRNA-processing protein PNO1 |
| Spipo1G0126300 | 5 | 1371.4 | 293.1 | 60S ribosomal protein L10-like protein |
| Spipo19G0027700 | 29 | 6951.7 | 241.3 | Ribulose bisphosphate carboxylase small chain |
| Spipo23G0013400 | 5 | 476.1 | 93.1 | Ribulose-1 5-bisphosphate carboxylase/oxygenase activase |

TABLE 5

FPKM for Turion-specific genes and DE transcriptional factors.

| Gene ID | Fold change | Frond FPKM | Turion FPKM | Directionality | Annotation |
|---|---|---|---|---|---|
| Spipo14G0001200 | NA | 0.0 | 31.0 | up-regulated | Late embryogenesis abundant protein LEA |
| Spipo5G0015500 | NA | 0.0 | 45.8 | up-regulated | Late embryogenesis abundant protein LEA |
| Spipo0G0166800 | 170 | 1.4 | 235.2 | up-regulated | Late embryogenesis abundant protein LEA |
| Spipo1G0033500 | 34 | 3.4 | 114.8 | up-regulated | Late embryogenesis abundant protein LEA |
| Spipo26G0007700 | 17 | 8.4 | 140.0 | up-regulated | Late embryogenesis abundant protein LEA |
| Spipo4G0008600 | 5 | 6.1 | 33.1 | up-regulated | bZIP transcription factor A |
| Spipo8G0037600 | 11 | 1.1 | 11.6 | up-regulated | Heat shock transcription factor A2 |
| Spipo9G0002000 | 5 | 14.2 | 67.8 | up-regulated | Heat shock transcription factor A2 |
| Spipo0G0155100 | 13 | 1.7 | 21.5 | up-regulated | Ethylene-responsive transcription factor 1 |
| Spipo3G0031800 | 7 | 10.3 | 74.2 | up-regulated | Ethylene-responsive transcription factor 2 |
| Spipo20G0027700 | 5 | 10.6 | 53.1 | up-regulated | Ethylene-responsive transcription factor 3 |
| Spipo11G0028200 | 7 | 32.7 | 4.4 | down-regulated | Ethylene-responsive transcription factor 4 |
| Spipo8G0045500 | 7 | 11.3 | 1.7 | down-regulated | WRKY transcription factor, putative |
| Spipo2G0055800 | 4 | 17.1 | 4.0 | down-regulated | bZIP transcription factor I |

TABLE 6

Functional GO enrichment in developing turions.

| Enriched GO ID | description |
| --- | --- |
| GO: 0001561 | fatty acid alpha-oxidation |
| GO: 0033539 | fatty acid beta-oxidation using acyl-CoA dehydrogenase |
| GO: 0010167 | response to nitrate |
| GO: 0015706 | nitrate transport |
| GO: 0055114 | oxidation-reduction process |
| GO: 0009830 | cell wall modification involved in abscission |
| GO: 0009651 | response to salt stress |
| GO: 0010106 | cellular response to iron ion starvation |
| GO: 0010150 | leaf senescence |
| GO: 0009737 | response to abscisic acid stimulus |
| GO: 0006826 | iron ion transport |
| GO: 0001676 | long-chain fatty acid metabolic process |
| GO: 0001666 | response to hypoxia |
| GO: 0046487 | glyoxylate metabolic process |
| GO: 0071732 | cellular response to nitric oxide |
| GO: 0010286 | heat acclimation |
| GO: 0071446 | cellular response to salicylic acid stimulus |
| GO: 0072329 | monocarboxylic acid catabolic process |
| GO: 0019579 | aldaric acid catabolic process |
| GO: 0009751 | response to salicylic acid stimulus |
| GO: 0042542 | response to hydrogen peroxide |
| GO: 0046686 | response to cadmium ion |
| GO: 0009788 | negative regulation of abscisic acid mediated signaling pathway |
| GO: 0009414 | response to water deprivation |

Abbreviations

ABA: abscisic acid; FPKM: Fragments Per Kilobase of transcript per Million mapped reads; DE gene: differentially expressed genes; LEA: late embryogenesis abundant protein; ABF: ABA-responsive element binding factors; ERF: Ethylene-responsive element binding factors; CPK: calcium-dependent protein kinase; MAPK: mitogen-activated protein kinase; CCR: Cinnamoyl-CoA reductase; CAD: cinnamyl-alcohol dehydrogenase; APS: ADP-glucose pyrophosphorylase small subunit; APL: ADP-glucose pyrophosphorylase large subunit; SS: starch synthase; GBSS: Granule-bound starch synthase; BE: Starch branching enzyme; DBE: Starchdebranching enzyme; ACCase: Acetyl-CoA carboxylase; GPAT: Glycerol-3-phosphate acyltransferase; AGPAT: Acylglycerophosphateacyltransferase; DGAT: Diacylglycerolacyltransferase.

TABLE S1

| Gene ID | Fold change | Frond FPKM | Turion FPKM | Directionality | Annotation | ABRE | ERE | GO | Function |
| --- | --- | --- | --- | --- | --- | --- | --- | --- | --- |
| Spipo14G0001200 | NA | 0.0 | 31.0 | up-regulated | Late embryogenesis abundant protein LEA | NO | YES | | |
| Spipo5G0015500 | NA | 0.0 | 45.8 | up-regulated | Late embryogenesis abundant protein LEA | YES | YES | | |
| Spipo0G0166800 | 170 | 1.4 | 235.2 | up-regulated | Late embryogenesis abundant protein LEA | NO | NO | | |
| Spipo6G0001100 | 146 | 0.3 | 45.3 | up-regulated | Peripheral-type benzodiazepine receptor | NO | YES | GO: 0009737 | response to abscisic acid stimulus |
| Spipo10G0013800 | 99 | 0.1 | 9.5 | up-regulated | 70 kDa heat shock protein | NO | YES | | |
| Spipo21G0043200 | 97 | 0.7 | 66.3 | up-regulated | Protein of unknown function, DUF599 | NO | YES | | |
| Spipo25G0008400 | 95 | 0.2 | 18.0 | up-regulated | myb domain protein 73 | NO | NO | | |
| Spipo2G0010600 | 84 | 0.2 | 19.7 | up-regulated | UDP-Glycosyltransferase superfamily | NO | NO | | |
| Spipo2G0035100 | 72 | 0.3 | 18.2 | up-regulated | Unknown protein | NO | YES | | |
| Spipo1G0017700 | 71 | 0.5 | 34.3 | up-regulated | (R)-limonene synthase, putative | NO | NO | | |
| Spipo8G0046200 | 67 | 0.2 | 15.6 | up-regulated | Protein phosphatase 2c, putative | YES | YES | GO: 0009788 | negative regulation of abscisic acid mediated signaling pathway |
| Spipo13G0026700 | 58 | 4.9 | 285.5 | up-regulated | Sulfite oxidase | NO | NO | | |
| Spipo5G0029200 | 57 | 0.8 | 48.1 | up-regulated | Major facilitator superfamily protein | NO | NO | GO: 0009737 | response to abscisic acid stimulus |
| Spipo2G0043800 | 54 | 6.4 | 340.8 | up-regulated | UDP-Glycosyltransferase superfamily | NO | YES | | |
| Spipo16G0044000 | 52 | 0.2 | 8.8 | up-regulated | UDP-Glycosyltransferase superfamily | NO | YES | | |
| Spipo11G0050900 | 49 | 20.2 | 986.4 | up-regulated | Kunitz trypsin inhibitor | NO | YES | | |
| Spipo19G0014500 | 43 | 0.5 | 22.4 | up-regulated | Galactinol synthase | NO | NO | GO: 0009737 | response to abscisic acid stimulus |
| Spipo4G0003000 | 42 | 0.5 | 22.8 | up-regulated | Glutamate decarboxylase, putative | NO | YES | | |
| Spipo25G0001000 | 42 | 1.0 | 42.4 | up-regulated | Exostosin family protein | NO | YES | | |
| Spipo14G0016400 | 41 | 0.8 | 33.7 | up-regulated | Lachrymatory-factor synthase | NO | NO | | |
| Spipo3G0013100 | 38 | 0.5 | 20.2 | up-regulated | NAC domain-containing protein 67 | NO | NO | GO: 0009788 | negative regulation of abscisic acid mediated signaling pathway |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo2G0039000 | 38 | 0.4 | 13.6 | up-regulated | UDP-Glycosyltransferase superfamily protein | NO | NO | | |
| Spipo1G0033500 | 34 | 3.4 | 114.8 | up-regulated | Late embryogenesis abundant protein LEA | NO | YES | | |
| Spipo15G0020300 | 34 | 1.5 | 52.2 | up-regulated | Cytochrome P450 | NO | NO | | |
| Spipo12G0048100 | 33 | 0.0 | 1.6 | up-regulated | Pentatricopeptide repeat-containing protein, putative | NO | YES | | |
| Spipo10G0053200 | 33 | 0.1 | 3.6 | up-regulated | Sucrose phosphate synthase | NO | NO | | |
| Spipo23G0012800 | 32 | 1.1 | 34.2 | up-regulated | Protein phosphatase 2C | NO | YES | GO: 0009788 | negative regulation of abscisic acid mediated signaling pathway |
| Spipo30G0012600 | 31 | 2.8 | 89.1 | up-regulated | Unknown protein | NO | YES | | |
| Spipo9G0021500 | 29 | 0.7 | 19.2 | up-regulated | Nucleotide-sugar transporter family protein | YES | NO | | |
| Spipo12G0044900 | 29 | 0.4 | 11.1 | up-regulated | CBL-interacting protein kinase 9 | YES | YES | | |
| Spipo0G0148600 | 27 | 23.1 | 635.9 | up-regulated | Unknown protein | NO | NO | | |
| Spipo15G0047700 | 27 | 0.1 | 1.6 | up-regulated | Cytochrome P450 | NO | YES | | |
| Spipo0G0175800 | 2.1 | 1.4 | 28.2 | up-regulated | EC metallothionein-like protein | NO | YES | | |
| Spipo0G0138500 | 19 | 10.6 | 206.5 | up-regulated | Unknown protein | YES | YES | | |
| Spipo4G0033500 | 19 | 0.1 | 1.0 | up-regulated | Pentatricopeptide repeat-containing protein, putative | NO | NO | | |
| Spipo2G0012200 | 19 | 0.4 | 7.8 | up-regulated | Glutamate dehydrogenase | NO | YES | | |
| Spipo4G0112100 | 19 | 1.6 | 31.2 | up-reglated | 9-cis-epoxycarotenoid dioxygenase 1 | NO | NO | | |
| Spipo1G0101000 | 18 | 0.1 | 1.6 | up-regulated | Pentatricopeptide repeat-containing protein | NO | YES | | |
| Spipo21G0039100 | 18 | 12.7 | 232.4 | up-regulated | Unknown protein | NO | NO | | |
| Spipo26G0007700 | 17 | 8.4 | 140.0 | up-regulated | Late embryogenesis abundant protein LEA | YES | YES | GO: 0009737 | response to abscisic acid stimulus |
| Spipo10G0023800 | 17 | 0.8 | 13.8 | up-regulated | Class 1 heat shock protein | NO | NO | | |
| Spipo14G0034300 | 16 | 3.9 | 62.6 | up-regulated | UDP glycosyltransferase | YES | NO | | |
| Spipo9G0006300 | 16 | 2.1 | 32.6 | up-regulated | Phosphoserine aminotransferase | NO | NO | | |
| Spipo8G0058900 | 16 | 1.2 | 19.4 | up-regulated | Flowering locus T/Terminal flower 1-like protein | NO | YES | GO: 0009737 | response to abscisic acid stimulus |
| Spipo1G0068300 | 15 | 8.6 | 133.2 | up-regulated | Heavy metal transport/detoxification superfamily protein | YES | YES | | |
| Spipo4G0016300 | 15 | 15.2 | 235.2 | up-regulated | Annexin | NO | NO | GO: 0009737 | response to abscisic acid stimulus |
| Spipo2G0064500 | 15 | 3.6 | 56.0 | up-regulated | Cytochrome P450 | NO | YES | | |
| Spipo6G0047600 | 15 | 0.7 | 10.1 | up-regulated | Beta glucosidase like protein | NO | NO | | |
| Spipo28G0015900 | 15 | 0.1 | 1.6 | up-regulated | Trehalose-6-phosphate synthase | NO | YES | | |
| Spipo18G0029800 | 15 | 28.7 | 420.3 | up-regulated | O-acetyltransferase-like | NO | NO | GO: 0009737 | response to abscisic acid stimulus |
| Spipo1G0076000 | 14 | 0.6 | 8.6 | up-regulated | Putative lysine decarboxylase family protein | NO | NO | | |
| Spipo8G0061900 | 14 | 4.6 | 64.7 | up-regulated | LOB domain-containing protein, putative | YES | YES | | |
| Spipo11G0038800 | 14 | 0.9 | 13.4 | up-regulated | *Arabidopsis* protein of unknown function (DUF241) | NO | YES | | |
| Spipo3G0078900 | 14 | 0.4 | 6.2 | up-regulated | Stachyose synthase, putative | YES | NO | GO: 0009737 | response to abscisic acid stimulus |
| Spipo18G0020700 | 14 | 10.6 | 143.8 | up-regulated | Formate dehydrogenase | NO | NO | | |
| Spipo4G0080100 | 13 | 0.2 | 2.3 | up-regulated | Cytochrome P450, putative | NO | YES | | |
| Spipo0G0155100 | 13 | 1.7 | 21.5 | up-regulated | Ethylene-responsive transcription factor 1 | YES | YES | GO: 0009737 | response to abscisic acid stimulus |
| Spipo28G0001000 | 13 | 3.3 | 42.3 | up-regulated | Phosphofructokinase, putative | NO | YES | | |
| Spipo15G0037300 | 13 | 3.8 | 48.6 | up-regulated | Mitogen-activated protein kinase kinase 1 (MAPK) | NO | YES | | |
| Spipo2G0067900 | 12 | 0.3 | 4.0 | up-regulated | Heat shock 70 kDa protein 1 | NO | YES | | |
| Spipo26G0000300 | 12 | 6.6 | 79.8 | up-regulated | unknown protein | NO | YES | | |
| Spipo2G0124000 | 12 | 0.6 | 7.7 | up-regulated | UDP-Glycosyltransferase superfamily protein | NO | NO | | |
| Spipo4G0079600 | 12 | 30.7 | 364.1 | up-regulated | 12-oxophytodienoate reductase | NO | YES | | |
| Spipo2G0096800 | 12 | 13.9 | 160.7 | up-regulated | unknown protein | NO | YES | | |
| Spipo1G0074600 | 11 | 22.6 | 257.1 | up-regulated | Unknown protein | NO | YES | | |
| Spipo7G0045000 | 11 | 12.2 | 137.5 | up-regulated | Sucrose phosphate synthase | NO | YES | | |
| Spipo8G0037600 | 11 | 1.1 | 11.6 | up-regulated | heat shock transcription factor A2 | NO | YES | | |

TABLE S1-continued

| Gene ID | Fold change | Frond FPKM | Turion FPKM | Direction-ality | Annotation | ABRE | ERE | GO | Function |
|---|---|---|---|---|---|---|---|---|---|
| Spipo21G0039300 | 11 | 3.2 | 35.0 | up-regulated | Unknown protein | NO | NO | | |
| Spipo5G0014300 | 11 | 3.4 | 36.1 | up-regulated | UDP-Glycosyltransferase superfamily protein | NO | YES | | |
| Spipo28G0003500 | 11 | 30.5 | 322.2 | up-regulated | Gibberellin-regulated protein | NO | YES | | |
| Spipo1G0058300 | 10 | 0.1 | 1.0 | up-regulated | Pentatricopeptide repeat-containing protein | NO | YES | | |
| Spipo3G0032200 | 10 | 10.4 | 105.2 | up-regulated | Epoxide hydrolase 1 | NO | YES | | |
| Spipo0G0116100 | 10 | 6.2 | 62.5 | up-regulated | Beta-glucosidase, putative | NO | YES | | |
| Spipo4G0092300 | 10 | 45.1 | 447.5 | up-regulated | Alcohol dehydrogenase | NO | YES | | |
| Spipo21G0022300 | 10 | 6.1 | 59.1 | up-regulated | Protein phosphatase 2c, putative | NO | YES | GO: 0009788 | negative regulation of abscisic acid mediated signaling pathway |
| Spipo19G0036000 | 10 | 1.2 | 11.2 | up-regulated | Aspartic proteinase, putative | NO | NO | | |
| Spipo19G0016500 | 10 | 2.8 | 27.3 | up-regulated | Isocitrate dehydrogenase [NADP] | NO | NO | | |
| Spipo0G0130700 | 9 | 1.6 | 15.5 | up-regulated | C4-dicarboxylate transporter/malic acid transport protein | NO | NO | GO: 0009737 | response to abscisic acid stimulus |
| Spipo7G0066600 | 9 | 164.7 | 1539.8 | up-regulated | Glyceraldehyde-3-phosphate dehydrogenase | YES | YES | | |
| Spipo22G0037200 | 9 | 18.8 | 173.7 | up-regulated | Amino acid selective channel protein | NO | NO | | |
| Spipo6G0047400 | 9 | 5.3 | 47.4 | up-regulated | Universal stress protein | NO | NO | | |
| Spipo25G0008100 | 9 | 1.5 | 13.5 | up-regulated | Alpha-mannosidase-like protein | NO | YES | | |
| Spipo5G0050700 | 9 | 0.6 | 5.3 | up-regulated | Sugar phosphate exchanger 2 | NO | NO | | |
| Spipo24G0000900 | 9 | 0.3 | 2.9 | up-regulated | Kinase, putative | NO | NO | | |
| Spipo2G0047500 | 8 | 17.8 | 148.0 | up-regulated | SAUR-like auxin-responsive protein family | YES | YES | | |
| Spipo11G0001500 | 8 | 22.3 | 185.3 | up-regulated | Abscisic acid 8'-hydroxylase 3 | NO | NO | | |
| Spipo5G0064900 | 8 | 10.7 | 88.2 | up-regulated | Tetratricopeptide repeat (TPR)-like superfamily protein | NO | YES | | |
| Spipo5G0040500 | 8 | 23.1 | 189.7 | up-regulated | Alpha-dioxygenase | NO | NO | GO: 0009737; GO: 0001561 | response to abscisic acid stimulus; fatty acid alpha-oxidation |
| Spipo27G0011300 | 8 | 13.8 | 112.1 | up-regulated | Beta-glucosidase A | NO | NO | | starch biosynthetic process |
| Spipo1G0069600 | 8 | 32.9 | 266.4 | up-regulated | 26S proteasome regulatory subunit S3, putative | NO | YES | | |
| Spipo11G0031500 | 8 | 3.9 | 31.8 | up-regulated | Cytochrome P450, putative | NO | NO | | |
| Spipo2G0040400 | 8 | 0.8 | 6.1 | up-regulated | Cytochrome P450 | YES | YES | | |
| Spipo11G0039200 | 8 | 5.8 | 45.4 | up-regulated | Alpha-amylase, putative | NO | YES | | |
| Spipo3G0041300 | 8 | 0.2 | 1.3 | up-regulated | Pentatricopeptide repeat-containing protein | NO | YES | | |
| Spipo14G0010200 | 8 | 1.8 | 13.9 | up-regulated | Protein CHUP1 | NO | YES | | |
| Spipo11G0060400 | 8 | 1.5 | 11.7 | up-regulated | Folate/biopterin transporter family protein | NO | YES | | |
| Spipo5G0023500 | 8 | 6.1 | 47.4 | up-regulated | Protein of unknown function (DUF1262) | NO | NO | | |
| Spipo1G0032700 | 8 | 11.8 | 91.9 | up-regulated | 2-succinylbenzoate-CoA ligase | NO | NO | | |
| Spipo16G0027000 | 8 | 4.4 | 33.4 | up-regulated | Glutathione-S-transferase (GST) | NO | YES | GO: 0019252 | starch biosynthetic process |
| Spipo0G0176700 | 8 | 0.6 | 4.9 | up-regulated | Ovate family protein 1 | NO | YES | | |
| Spipo18G0038500 | 8 | 36.0 | 291.5 | up-regulated | Glucose-1-phosphate adenylyltransferase | NO | NO | GO: 0019252 | starch biosynthetic process |
| Spipo11G0025200 | 7 | 2.1 | 15.6 | up-regulated | methionine gamma-lyase | NO | YES | | |
| Spipo13G0053800 | 7 | 6.9 | 51.6 | up-regulated | Glyceraldehyde 3-phosphate dehydrogenase | YES | NO | | |
| Spipo5G0077000 | 7 | 0.4 | 2.7 | up-regulated | Pentatricopeptide repeat-containing protein | NO | NO | | |
| Spipo23G0007500 | 7 | 1.5 | 10.9 | up-regulated | O-fucosyltransferase family protein | NO | NO | | |
| Spipo5G0054900 | 7 | 1.0 | 7.1 | up-regulated | Cytochrome P450, putative | YES | YES | | |
| Spipo29G0009400 | 7 | 3.4 | 24.9 | up-regulated | Dof zinc finger protein | NO | NO | | |
| Spipo7G0041900 | 7 | 1.4 | 9.8 | up-regulated | ABC transporter G family member | NO | YES | GO: 0009737 | response to abscisic acid stimulus |
| Spipo3G0031800 | 7 | 10.3 | 74.2 | up-regulated | Ethylene-responsive transcription factor 2 | NO | NO | GO: 0009737 | response to abscisic acid stimulus |
| Spipo21G0009000 | 7 | 4.7 | 33.4 | up-regulated | Auxin responsive protein | YES | YES | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo0G0124700 | 7 | 2.0 | 14.1 | up-regulated | G-type lectin S-receptor-like serine/threonine-protein kinase | NO | YES | | |
| Spipo19G0037600 | 7 | 21.2 | 144.8 | up-regulated | Hydroxyacylglutathione hydrolase | NO | YES | | |
| Spipo3G0073100 | 7 | 14.3 | 96.6 | up-regulated | Peroxiredoxin | NO | YES | | |
| Spipo22G0042300 | 7 | 24.8 | 166.4 | up-regulated | Soul heme-binding family protein | NO | YES | | |
| Spipo10G0025700 | 7 | 1.1 | 7.6 | up-regulated | Histidine decarboxylase | NO | NO | | |
| Spipo7G0061700 | 7 | 140.8 | 936.4 | up-regulated | Cysteine-rich secretory protein | NO | YES | | |
| Spipo18G0031500 | 7 | 2.8 | 18.8 | up-regulated | LOB domain-containing protein 41 | NO | YES | | |
| Spipo8G0027700 | 7 | 1.4 | 8.9 | up-regulated | MATE efflux family protein | YES | NO | | |
| Spipo28G0017100 | 7 | 1.6 | 10.6 | up-regulated | Cellulose-synthase-like C5 | NO | YES | | |
| Spipo0G0155000 | 6 | 1.5 | 9.8 | up-regulated | Cytochrome P450 flavonoid 3',5'-hydroxylase | NO | NO | | |
| Spipo7G0010700 | 6 | 10.1 | 64.8 | up-regulated | Dihydroflavonol 4-reductase | NO | YES | | |
| Spipo10G0000200 | 6 | 26.2 | 167.8 | up-regulated | Dihydroflavonol 4-reductase | NO | NO | | |
| Spipo15G0031400 | 6 | 3.3 | 21.1 | up-regulated | Major facilitator superfamily protein | NO | YES | | |
| Spipo0G0156500 | 6 | 15.5 | 97.9 | up-regulated | Alpha-dioxygenase | NO | NO | GO: 0009737; GO: 0001561 | response to abscisic acid stimulus; fatty acid alpha-oxidation |
| Spipo1G0110400 | 6 | 5.8 | 36.8 | up-regulated | Electron transfer flavoprotein-ubiquinone oxidoreductase | NO | NO | GO: 0033539 | fatty acid beta-oxidation |
| Spipo6G0053900 | 6 | 6.5 | 39.9 | up-regulated | Major facilitator superfamily antiporter, putative, expressed | NO | NO | | |
| Spipo8G0062500 | 6 | 7.2 | 44.3 | up-regulated | Receptor-like protein kinase | NO | YES | GO: 0009737 | response to abscisic acid stimulus |
| Spipo14G0009000 | 6 | 1.7 | 10.6 | up-regulated | Major facilitator superfamily protein | NO | NO | | |
| Spipo15G0028800 | 6 | 2.5 | 15.1 | up-regulated | Cysteine-rich receptor-like protein kinase | NO | YES | | |
| Spipo28G0011200 | 6 | 2.3 | 13.5 | up-regulated | Chaperone clpb, putative | NO | NO | | |
| Spipo5G0051100 | 6 | 7.8 | 46.5 | up-regulated | Cytochrome P450, putative | NO | YES | | |
| Spipo11G0020200 | 6 | 116.8 | 695.6 | up-regulated | Kunitz trypsin inhibitor 4 | NO | NO | | |
| Spipo1G0021700 | 6 | 3.2 | 18.9 | up-regulated | Protein phosphatase 2c, putative | NO | YES | GO: 0009788 | negative regulation of abscisic acid mediated signaling pathway |
| Spipo7G0059600 | 6 | 28.6 | 168.7 | up-regulated | AP-1 complex subunit gamma-2, putative | NO | NO | | |
| Spipo3G0031300 | 6 | 16.3 | 95.9 | up-regulated | Acyl-CoA dehydrogenase | NO | YES | GO: 0033539 | fatty acid beta-oxidation |
| Spipo26G0019100 | 6 | 3.1 | 17.7 | up-regulated | Integral membrane protein TmpA | NO | YES | | |
| Spipo8G0065700 | 6 | 1.2 | 6.9 | up-regulated | Core-2/I-branching beta-1,6-N-acetylglucosaminyltransferase family protein | NO | NO | | |
| Spipo17G0009300 | 6 | 1.5 | 8.7 | up-regulated | CBS domain-containing protein, putative, expressed | YES | YES | | |
| Spipo10G0038500 | 6 | 2.1 | 12.1 | up-regulated | Phosphatidylinositol kinase family-like protein | NO | YES | | |
| Spipo0G0180000 | 6 | 98.0 | 561.3 | up-regulated | Alpha-dioxygenase | NO | NO | GO: 0009737; GO: 0001561 | response to abscisic acid stimulus; fatty acid alpha-oxidation |
| Spipo24G0001200 | 6 | 5.6 | 31.8 | up-regulated | Adiponectin receptor protein | NO | NO | | |
| Spipo10G0030200 | 6 | 11.2 | 63.7 | up-regulated | Chaperone DnaJ-domain superfamily protein | YES | YES | | |
| Spipo8G0040300 | 6 | 1.9 | 10.8 | up-regulated | 3-hydroxyisobutyrate dehydrogenase | NO | NO | | |
| Spipo23G0017700 | 6 | 1.6 | 9.0 | up-regulated | GTPaseobg | NO | NO | | |
| Spipo0G0148500 | 6 | 34.3 | 192.2 | up-regulated | Unknown protein | NO | YES | | |
| Spipo16G0046000 | 5 | 17.7 | 96.7 | up-regulated | Beta-amylase | YES | YES | | |
| Spipo3G0073400 | 5 | 5.0 | 27.4 | up-regulated | tolB protein-related | NO | NO | | |
| Spipo4G0008600 | 5 | 6.1 | 33.1 | up-regulated | bZIP transcription factor A | NO | NO | | |
| Spipo3G0064800 | 5 | 14.2 | 76.7 | up-regulated | Beta-1,3-glucanase | NO | NO | | |
| Spipo0G0156600 | 5 | 19.5 | 104.4 | up-regulated | Prostaglandin G/H synthase | NO | NO | GO: 0009737; GO: 0001561 | response to abscisic acid stimulus; fatty acid alpha-oxidation |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo11G0043800 | 5 | 10.3 | 54.6 | up-regulated | Calcium-binding EF hand family protein | NO | YES | | |
| Spipo23G0006300 | 5 | 7.3 | 38.4 | up-regulated | RNA-binding protein | YES | YES | | |
| Spipo12G0062400 | 5 | 2.8 | 14.6 | up-regulated | Glycogen debranching enzyme | NO | YES | GO: 0019252 | starch biosynthetic process |
| Spipo18G0028400 | 5 | 0.8 | 3.9 | up-regulated | NHL domain-containing protein | NO | YES | | |
| Spipo7G0060200 | 5 | 8.5 | 44.3 | up-regulated | Unknown protein | NO | YES | | |
| Spipo10G0017900 | 5 | 5.8 | 30.4 | up-regulated | ABC transporter G family member | NO | YES | | |
| Spipo2G0099700 | 5 | 1.4 | 7.5 | up-regulated | unknown protein | NO | NO | | |
| Spipo11G0031600 | 5 | 2.9 | 15.1 | up-regulated | Cytochrome P450 | NO | NO | | |
| Spipo16G0030600 | 5 | 4.1 | 21.5 | up-regulated | Glutamine synthetase | NO | NO | | |
| Spipo2G0061100 | 5 | 3.4 | 17.5 | up-regulated | Prolyl 4-hydroxylase alpha subunit, putative | NO | YES | | |
| Spipo20G0017000 | 5 | 4.5 | 22.9 | up-regulated | Isoflavonereductase-like protein | NO | NO | | |
| Spipo4G0013100 | 5 | 55.2 | 282.1 | up-regulated | Inositol-3-phosphate synthase | NO | YES | | |
| Spipo4G0033200 | 5 | 18.5 | 94.4 | up-regulated | MtN19-like protein | NO | YES | | |
| Spipo14G0054900 | 5 | 2.0 | 9.9 | up-regulated | Dihydroflavonol 4-reductase | NO | YES | | |
| Spipo2G0071700 | 5 | 0.4 | 1.9 | up-regulated | Pentatricopeptide repeat-containing protein, putative | NO | YES | | |
| Spipo0G0030300 | 5 | 47.3 | 238.4 | up-regulated | Aldehyde dehydrogenase | YES | YES | | |
| Spipo3G0002000 | 5 | 1.6 | 7.8 | up-regulated | Xanthine/uracil permease family protein | YES | YES | | |
| Spipo20G0027700 | 5 | 10.6 | 53.1 | up-regulated | Ethylene-responsive transcription factor 3 | NO | NO | | |
| Spipo7G0013600 | 5 | 8.2 | 40.9 | up-regulated | 2-oxoglutarate (2OG) and Fe(II)-dependent oxygenase superfamily | NO | NO | | |
| Spipo0G0013700 | 5 | 2.4 | 12.0 | up-regulated | Unknown protein | YES | YES | | |
| Spipo2G0018300 | 5 | 9.6 | 47.7 | up-regulated | Early light-induced protein | NO | NO | | |
| Spipo7G0048800 | 5 | 16.7 | 82.8 | up-regulated | NAC domain protein | NO | YES | | |
| Spipo8G0040000 | 5 | 1.2 | 5.5 | up-regulated | 2-hydroxy-3-oxopropionate reductase | NO | YES | | |
| Spipo9G0002000 | 5 | 14.2 | 67.8 | up-regulated | Heat shock transcription factor A-2 | NO | NO | | |
| Spipo9G0033600 | 5 | 123.3 | 585.4 | up-regulated | Fructose-bisphosphatealdolase | NO | YES | | |
| Spipo23G0001600 | 5 | 3.2 | 15.2 | up-regulated | Kinase, pfkB family protein, expressed | NO | YES | | |
| Spipo7G0044000 | 5 | 4.4 | 20.5 | up-regulated | Cellulose synthase-like B3 | YES | YES | | |
| Spipo6G0053800 | 5 | 3.7 | 17.3 | up-regulated | Major facilitator superfamily antiporter, putative, expressed | NO | NO | | |
| Spipo2G0077900 | 5 | 6.1 | 28.4 | up-regulated | UDP-Glycosyltransferase superfamily | NO | NO | | |
| Spipo14G0026800 | 5 | 4.0 | 18.3 | up-regulated | Eukaryotic aspartyl protease family protein | NO | YES | GO: 0009737 | response to abscisic acid stimulus |
| Spipo0G0179100 | 5 | 11.5 | 53.2 | up-regulated | Electron transfer flavoprotein-ubiquinone oxidoreductase | NO | YES | GO: 0033539 | fatty acid beta-oxidation |
| Spipo1G0003700 | 5 | 7.6 | 35.1 | up-regulated | Calcium-dependent protein kinase (CPK) | YES | NO | | |
| Spipo15G0048400 | 5 | 7.7 | 34.9 | up-regulated | Cathepsin L-like cysteine proteinase | NO | YES | | |
| Spipo0G0154800 | 5 | 4.4 | 19.7 | up-regulated | Xanthine dehydrogenase/oxidase | NO | YES | | |
| Spipo2G0033500 | 4 | 7.7 | 34.6 | up-regulated | Lysine-ketoglutaratereductase/saccharopine dehydrogenase | NO | NO | | |
| Spipo4G0038800 | 4 | 3.9 | 17.3 | up-regulated | GDSL esterase/lipase | NO | NO | | |
| Spipo13G0039800 | 4 | 16.2 | 70.6 | up-regulated | Cytochrome P450 | NO | NO | | |
| Spipo3G0073500 | 4 | 2.9 | 12.4 | up-regulated | tolB protein-related | NO | NO | | |
| Spipo7G0066500 | 4 | 1.6 | 6.9 | up-regulated | Multidrug resistance protein ABC transporter family | YES | YES | | |
| Spipo24G0015900 | 4 | 2.8 | 12.2 | up-regulated | Unknown protein | NO | NO | | |
| Spipo9G0002200 | 4 | 105.3 | 452.4 | up-regulated | Thioredoxin | NO | YES | | |
| Spipo12G0003900 | 4 | 37.9 | 162.9 | up-regulated | Myb domain protein 73 | NO | YES | GO: 0009737 | response to abscisic acid stimulus |
| Spipo2G0096700 | 4 | 55.9 | 238.4 | up-regulated | Peroxidase 73, putative | NO | YES | | |
| Spipo26G0017500 | 4 | 5.7 | 24.1 | up-regulated | Exostosin family protein | NO | YES | | |
| Spipo7G0028500 | 4 | 23.1 | 97.9 | up-regulated | Potassium transporter 11 | NO | NO | | |
| Spipo5G0012100 | 4 | 17.9 | 75.8 | up-regulated | CCR4-NOT transcription complex subunit 7 | NO | YES | | |
| Spipo19G0030800 | 4 | 6.0 | 25.1 | up-regulated | Inositol-pentakisphosphate 2-kinase, putative | NO | NO | | |
| Spipo20G0012400 | 4 | 1.5 | 6.2 | up-regulated | RING/U-box superfamily protein | NO | YES | | |
| Spipo23G0021500 | 4 | 5.4 | 22.8 | up-regulated | SEC14 cytosolic factor family protein/phosphoglyceride transfer family protein | NO | YES | | |
| Spipo22G0012700 | 4 | 31.1 | 130.2 | up-regulated | Rubber elongation factor protein (REF) | NO | YES | | |
| Spipo18G0007900 | 4 | 70.2 | 289.4 | up-regulated | Aspartate aminotransferase | NO | YES | | |
| Spipo0G0085700 | 4 | 14.1 | 57.9 | up-regulated | Unknown protein | NO | NO | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo16G0033600 | 4 | 2.5 | 10.2 | up-regulated | Alpha-galactosidase 1 | YES | NO | | |
| Spipo3G0022400 | 4 | 11.3 | 46.0 | up-regulated | Glutathione-S-transferase (GST) | NO | YES | | |
| Spipo6G0056800 | 4 | 11.5 | 46.5 | up-regulated | NAC domain-containing protein 67 | YES | YES | GO: 0009788 | negative regulation of abscisic acid mediated signaling pathway |
| Spipo3G0033300 | 4 | 8.9 | 35.9 | up-regulated | Protein of unknown function, DUF538 | NO | NO | | |
| Spipo5G0073900 | 4 | 9.2 | 37.0 | up-regulated | Alternative oxidase | NO | YES | | |
| Spipo12G0023200 | 4 | 0.5 | 1.9 | up-regulated | Disease resistance protein | NO | NO | | |
| Spipo11G0033800 | 69 | 33.6 | 0.5 | down-regulated | Aquaporin | NO | NO | | |
| Spipo17G0047900 | 66 | #### | 1921.3 | down-regulated | Chitobiosyldiphosphodolichol beta-mannosyltransferase | YES | YES | | |
| Spipo1G0071900 | 54 | #### | 1538.8 | down-regulated | Chitobiosyldiphosphodolichol beta-mannosyltransferase | NO | YES | | |
| Spipo13G0047300 | 50 | 608.3 | 12.1 | down-regulated | Ycf68 protein | NO | NO | | |
| Spipo12G0026200 | 50 | 8.6 | 0.2 | down-regulated | Eukaryotic aspartyl protease family protein | YES | YES | | |
| Spipo1G0120500 | 45 | 72.3 | 1.6 | down-regulated | Lectin | NO | YES | | |
| Spipo0G0129700 | 38 | 103.0 | 2.7 | down-regulated | Bifunctional inhibitor/lipid-transfer protein/seed storage 2S albumin superfamily | NO | YES | | |
| Spipo1G0120400 | 37 | 27.1 | 0.7 | down-regulated | Lectin | NO | NO | | |
| Spipo26G0006100 | 36 | 27.7 | 0.8 | down-regulated | BURP domain-containing protein | NO | NO | | |
| Spipo1G0108500 | 35 | 44.8 | 1.3 | down-regulated | Unknown protein | NO | NO | | |
| Spipo14G0020800 | 30 | 498.4 | 16.6 | down-regulated | Arabinogalactan peptide 20-like | YES | YES | | |
| Spipo19G0027700 | 29 | #### | 241.3 | down-regulated | Ribulosebisphosphate carboxylase small chain | NO | NO | | |
| Spipo21G0033600 | 27 | #### | 487.3 | down-regulated | Oxidative stress 3 | NO | NO | | |
| Spipo1G0121700 | 26 | 1530.8 | 59.8 | down-regulated | Bifunctional inhibitor/lipid-transfer protein/seed storage 2S albumin superfamily | NO | NO | | |
| Spipo23G0012000 | 25 | 6197.7 | 243.6 | down-regulated | Unknown protein | NO | YES | | |
| Spipo0G0022100 | 24 | 51.0 | 2.1 | down-regulated | Protein of unknown function, DUF538 | NO | NO | | |
| Spipo7G0031300 | 24 | 184.7 | 7.7 | down-regulated | Unknown protein | NO | NO | | |
| Spipo6G0029000 | 22 | 15.6 | 0.7 | down-regulated | O-acyltransferase WSD1 | YES | NO | | |
| Spipo0G0067700 | 22 | 309.9 | 14.0 | down-regulated | Unknown protein | NO | YES | | |
| Spipo2G0110300 | 22 | 28.5 | 1.3 | down-regulated | Cysteine-rich secretory protein | NO | NO | | |
| Spipo1G0078600 | 21 | 19.1 | 0.9 | down-regulated | Peroxidase | NO | NO | | |
| Spipo12G0010100 | 20 | 7.7 | 0.4 | down-regulated | Nucleobaseascorbate transporter | NO | NO | | |
| Spipo18G0014800 | 20 | 95.2 | 4.9 | down-regulated | FASCICLIN-like arabinogalactan 6 | NO | YES | | |
| Spipo6G0002600 | 19 | 503.1 | 26.1 | down-regulated | Unknown protein | NO | NO | | |
| Spipo3G0074100 | 19 | 11.9 | 0.6 | down-regulated | fucosyltransferase 1 | NO | YES | | |
| Spipo5G0036600 | 19 | 1.7 | 0.1 | down-regulated | Receptor kinase | NO | YES | | |
| Spipo10G0007200 | 19 | 7698.9 | 414.6 | down-regulated | Unknown protein | NO | NO | | |
| Spipo11G0017100 | 18 | 19.8 | 1.1 | down-regulated | Blue copper protein | NO | YES | | |
| Spipo8G0067000 | 17 | 11.2 | 0.7 | down-regulated | Unknown protein | YES | YES | | |
| Spipo14G0059300 | 17 | 323.8 | 19.5 | down-regulated | Bifunctional inhibitor/lipid-transfer protein/seed storage 2S albumin-like protein | NO | NO | | |
| Spipo1G0007400 | 16 | 258.6 | 16.6 | down-regulated | Unknown protein | NO | NO | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo0G0159700 | 15 | 108.2 | 7.2 | down-regulated | BURP domain-containing protein | NO | NO | | |
| Spipo3G0024800 | 14 | 1018.4 | 71.2 | down-regulated | Pre-rRNA-processing protein PNO1 | NO | NO | | |
| Spipo9G0045500 | 14 | 30.0 | 2.2 | down-regulated | Carboxyvinyl-carboxyphosphonate-phosphorylmutase, putative, expressed | NO | NO | | |
| Spipo9G0031000 | 13 | 5.1 | 0.4 | down-regulated | Kinase, putative | NO | YES | | |
| Spipo5G0017800 | 13 | 1348.5 | 105.8 | down-regulated | Unknown protein | NO | NO | | |
| Spipo8G0062200 | 12 | 11.6 | 0.9 | down-regulated | Protein kinase family protein | NO | YES | | |
| Spipo0G0025800 | 12 | 5.8 | 0.5 | down-regulated | Leucine-rich repeat protein kinase-like protein | NO | NO | | |
| Spipo26G0006600 | 12 | 68.2 | 5.9 | down-regulated | BURP domain-containing protein | YES | NO | | |
| Spipo20G0016500 | 11 | 64.9 | 5.8 | down-regulated | Plant cadmium resistance 2 | NO | YES | | |
| Spipo7G0011900 | 11 | 33.1 | 3.1 | down-regulated | Early nodulin 20, putative | NO | NO | | |
| Spipo20G0037200 | 11 | #### | 1037.5 | down-regulated | Unknown protein | NO | YES | | |
| Spipo30G0013100 | 10 | 3.4 | 0.3 | down-regulated | Protein kinase family protein | NO | YES | | |
| Spipo8G0009900 | 10 | 15.2 | 1.5 | down-regulated | Peroxidase 39 | NO | NO | | |
| Spipo0G0134100 | 10 | 4.7 | 0.5 | down-regulated | Protein kinase family protein | NO | NO | | |
| Spipo2G0109900 | 10 | 141.9 | 14.4 | down-regulated | CAP (Cysteine-rich secretory proteins and Pathogenesis-related 1 protein) | NO | NO | | |
| Spipo0G0190200 | 10 | 486.5 | 49.4 | down-regulated | Purple acid phosphatase 1 | NO | NO | | |
| Spipo10G0029700 | 10 | 2.4 | 0.2 | down-regulated | Disease resistance gene homolog 9N | NO | NO | | |
| Spipo30G0015100 | 9 | 7.6 | 0.8 | down-regulated | 9-cis-epoxycarotenoid dioxygenase 1 | NO | YES | | |
| Spipo28G0025100 | 9 | 21.4 | 2.3 | down-regulated | Cation transport regulator-like protein | YES | YES | | |
| Spipo2G0091100 | 9 | 7.1 | 0.8 | down-regulated | Unknown protein | NO | YES | | |
| Spipo2G0100400 | 9 | 223.5 | 25.3 | down-regulated | Nucleotide-sugar transporter family protein | YES | YES | | |
| Spipo2G0110400 | 9 | 218.2 | 24.7 | down-regulated | Cysteine-rich secretory protein | NO | YES | | |
| Spipo5G0027100 | 9 | 18.7 | 2.1 | down-regulated | Myb domain protein 73 | YES | YES | | |
| Spipo1G0079200 | 9 | 14.9 | 1.7 | down-regulated | Peroxidase | NO | NO | | |
| Spipo14G0014700 | 9 | #### | 1293.9 | down-regulated | Unknown protein | NO | YES | | |
| Spipo4G0110100 | 9 | 58.4 | 6.8 | down-regulated | Fructose-1,6-bisphosphatase class 1 | YES | YES | | |
| Spipo19G0016700 | 8 | 1666.6 | 196.3 | down-regulated | Unknown protein | NO | YES | | |
| Spipo11G0063600 | 8 | 168.4 | 20.3 | down-regulated | Unknown protein | NO | YES | | |
| Spipo9G0030500 | 8 | 3.8 | 0.5 | down-regulated | Kinase, putative | NO | YES | | |
| Spipo14G0033900 | 8 | 5094.7 | 626.7 | down-regulated | Carbonic anhydrase | NO | YES | | |
| Spipo1G0023600 | 8 | 6.2 | 0.8 | down-regulated | HXXXD-type acyl-transferase family protein | NO | NO | | |
| Spipo1G0018600 | 8 | 52.1 | 6.6 | down-regulated | RING finger and CHY zinc finger domain-containing protein 1 | NO | NO | | |
| Spipo3G0031100 | 8 | 47.7 | 6.1 | down-regulated | Pectinesterase | NO | NO | | |
| Spipo7G0045100 | 8 | 855.2 | 109.7 | down-regulated | Unknown protein | NO | NO | | |
| Spipo13G0020200 | 8 | 433.6 | 56.5 | down-regulated | Phosphoglycolate phosphatase | YES | YES | | |
| Spipo0G0001400 | 8 | 4.2 | 0.6 | down-regulated | Cationic amino acid transporter | NO | YES | | |
| Spipo20G0013200 | 8 | 117.3 | 15.6 | down-regulated | Acid phosphatase, putative, expressed | NO | YES | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo3G0049000 | 7 | 127.9 | 18.6 | down-regulated | Glucose-1-phosphate adenylyltransferase | NO | NO | | |
| Spipo11G0028200 | 7 | 32.7 | 4.4 | down-regulated | Ethylene-responsive transcription factor 4 | NO | YES | | |
| Spipo8G0035200 | 7 | 71.3 | 9.6 | down-regulated | Putative nuclease HARBI1-like | NO | YES | | |
| Spipo0G0152100 | 7 | 15.2 | 2.1 | down-regulated | Beta-glucosidase-like glycosyl hydrolase | NO | NO | | |
| Spipo3G0031200 | 7 | 5.9 | 0.8 | down-regulated | Endo-1,4-beta-glucanase | NO | NO | | |
| Spipo0G0000400 | 7 | 108.8 | 15.0 | down-regulated | Short-chain dehydrogenase/reductase 2 | YES | YES | | |
| Spipo9G0039400 | 7 | 68.2 | 9.4 | down-regulated | Histone H3 | NO | NO | | |
| Spipo9G0045200 | 7 | 18.8 | 2.6 | down-regulated | Carboxyvinyl-carboxyphosphonate-phosphorylmutase | NO | YES | | |
| Spipo1G0125300 | 7 | 186.7 | 26.8 | down-regulated | Lectin | NO | NO | | |
| Spipo0G0046100 | 7 | 112.4 | 16.4 | down-regulated | Histone H3 | YES | YES | | |
| Spipo4G0069000 | 7 | 23.5 | 3.5 | down-regulated | Tyrosine-rich hydroxyproline-rich glycoprotein | NO | NO | | |
| Spipo10G0030500 | 7 | 7.2 | 1.1 | down-regulated | Subtilisin-like serine protease | NO | NO | | |
| Spipo8G0045500 | 7 | 11.3 | 1.7 | down-regulated | WRKY transcription factor, putative | NO | NO | | |
| Spipo18G0023200 | 7 | 13.3 | 2.0 | down-regulated | Naphthoate synthase, putative | NO | YES | | |
| Spipo0G0068600 | 7 | 168.0 | 25.6 | down-regulated | Fanconi anemia group I protein | NO | NO | | |
| Spipo32G0009000 | 7 | 83.6 | 12.8 | down-regulated | G-type lectin S-receptor-like serine/threonine-protein kinase | NO | YES | | |
| Spipo4G0061000 | 6 | 10.4 | 1.6 | down-regulated | GDSL esterase/lipase | NO | NO | | |
| Spipo7G0024900 | 6 | 2151.8 | 336.5 | down-regulated | Auxin-repressed protein | NO | NO | | |
| Spipo14G0048100 | 6 | 229.3 | 36.3 | down-regulated | Aminomethyltransferase | NO | NO | | |
| Spipo14G0022500 | 6 | 4.7 | 0.7 | down-regulated | Disease resistance protein (CC-NBS-LRR) | NO | NO | | |
| Spipo4G0004200 | 6 | 47.5 | 7.6 | down-regulated | Acid phosphatase, putative, expressed | NO | NO | | |
| Spipo29G0003800 | 6 | 24.4 | 3.9 | down-regulated | Heavy metal transport/detoxification superfamily protein | NO | YES | | |
| Spipo20G0028500 | 6 | 15.7 | 2.6 | down-regulated | Sulfate transporter | NO | NO | | |
| Spipo9G0012700 | 6 | 246.1 | 40.5 | down-regulated | Adenylosuccinatesynthetase | NO | NO | | |
| Spipo3G0061200 | 6 | 2685.1 | 442.0 | down-regulated | Chlorophyll a/b-binding protein | YES | NO | | |
| Spipo3G0041200 | 6 | 65.9 | 11.0 | down-regulated | CASP-like protein | YES | YES | | |
| Spipo0G0035400 | 6 | 33.9 | 5.7 | down-regulated | Pectinesterase | NO | NO | | |
| Spipo2G0072200 | 6 | 38.3 | 6.4 | down-regulated | Protein of unknown function, DUF642 | NO | NO | | |
| Spipo3G0023000 | 6 | 14.9 | 2.6 | down-regulated | Cyclin B1 | NO | YES | | |
| Spipo3G0026500 | 6 | 11.4 | 2.0 | down-regulated | Triacylglycerol lipase, putative | NO | YES | | |
| Spipo2G0093200 | 6 | 44.1 | 7.6 | down-regulated | Unknown protein | NO | NO | | |
| Spipo13G0007500 | 6 | 159.5 | 27.5 | down-regulated | Histone H3 | YES | YES | | |
| Spipo12G0058200 | 6 | 2360.0 | 407.0 | down-regulated | Xyloglucanendotransglucosylase/hydrolase | NO | NO | | |
| Spipo5G0067200 | 6 | 14.6 | 2.6 | down-regulated | Cellulose synthase-like protein | NO | YES | | |
| Spipo20G0004100 | 6 | 91.6 | 16.1 | down-regulated | Nucleoside diphosphate kinase | NO | NO | | |
| Spipo0G0015500 | 6 | 8.4 | 1.5 | down-regulated | Urea active transporter-like protein | NO | NO | | |
| Spipo29G0004700 | 6 | 10.5 | 1.9 | down-regulated | Cyclin B1 | NO | YES | | |
| Spipo2G0022100 | 6 | 1774.3 | 315.0 | down-regulated | Dynein light chain 1 cytoplasmic-like protein | NO | YES | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo8G0020200 | 6 | 651.1 | 117.2 | down-regulated | Thylakoid membrane phosphoprotein 14 kDa | NO | NO | | |
| Spipo3G0020200 | 5 | 21.1 | 3.8 | down-regulated | Alpha-L-arabinofuranosidase | YES | YES | | |
| Spipo1G0117200 | 5 | 117.9 | 21.5 | down-regulated | Laccase 11 | NO | NO | | |
| Spipo8G0039700 | 5 | 22.8 | 4.3 | down-regulated | Glucan endo-1,3-beta-glucosidase, putative | NO | YES | | |
| Spipo28G0019000 | 5 | 77.9 | 14.8 | down-regulated | Histone H4 | NO | YES | | |
| Spipo2G0093000 | 5 | 50.4 | 9.6 | down-regulated | Unknown protein | NO | YES | | |
| Spipo28G0012500 | 5 | 328.4 | 64.0 | down-regulated | Chaperone protein dnaJ | YES | YES | | |
| Spipo0G0114100 | 5 | 259.2 | 50.5 | down-regulated | Protodermal factor 1.3 | NO | YES | | |
| Spipo23G0013400 | 5 | 476.1 | 93.1 | down-regulated | Ribulose-1 5-bisphosphate carboxylase/oxygenaseactivase | NO | YES | | |
| Spipo12G0016000 | 5 | 10.2 | 2.0 | down-regulated | O-fucosyltransferase family protein | NO | YES | | |
| Spipo26G0012100 | 5 | 894.9 | 176.9 | down-regulated | Arabinogalactan protein 20 | NO | YES | | |
| Spipo31G0007300 | 5 | 3.4 | 0.7 | down-regulated | Leucine-rich repeat receptor-like protein kinase family protein | NO | NO | | |
| Spipo8G0005400 | 5 | 14.9 | 3.0 | down-regulated | Glutamate receptor | NO | NO | | |
| Spipo1G0080800 | 5 | 2505.2 | 507.5 | down-regulated | Unknown protein | YES | NO | | |
| Spipo3G0012100 | 5 | 5.4 | 1.1 | down-regulated | Protein kinase-like protein | NO | NO | | |
| Spipo20G0028600 | 5 | 9.6 | 2.0 | down-regulated | Sulfate transporter, putative | NO | NO | | |
| Spipo17G0045100 | 5 | 86.3 | 17.8 | down-regulated | Aquaporin | NO | YES | | |
| Spipo2G0059000 | 5 | 5.8 | 1.2 | down-regulated | Major facilitator superfamily protein | NO | YES | | |
| Spipo9G0038700 | 5 | 53.8 | 11.2 | down-regulated | U-box domain-containing protein | NO | NO | | |
| Spipo1G0126300 | 5 | #### | 293.1 | down-regulated | 60S ribosomal protein L10-like protein | NO | NO | | |
| Spipo3G0024100 | 5 | 24.6 | 5.3 | down-regulated | Nicotianamine synthase, putative | NO | NO | | |
| Spipo16G0011700 | 5 | 25.7 | 5.5 | down-regulated | L-lactate dehydrogenase | NO | NO | | |
| Spipo6G0071400 | 5 | 125.5 | 27.1 | down-regulated | Pectinacetylesterase family protein | NO | YES | | |
| Spipo22G0026300 | 5 | 186.4 | 40.4 | down-regulated | Expansin | NO | YES | | |
| Spipo2G0039900 | 5 | 15.3 | 3.3 | down-regulated | Amine oxidase, putative | NO | YES | | |
| Spipo2G0092600 | 5 | 66.7 | 14.6 | down-regulated | Early nodulin-like protein 17 | YES | YES | | |
| Spipo0G0183100 | 5 | 14.4 | 3.2 | down-regulated | Heparanase-like protein 2 | NO | YES | | |
| Spipo15G0035800 | 5 | 429.5 | 94.0 | down-regulated | Glutamine synthetase | NO | YES | | |
| Spipo17G0007500 | 5 | 101.0 | 22.2 | down-regulated | Methyltransferase type 11 | NO | YES | | |
| Spipo22G0045000 | 5 | 13.9 | 3.1 | down-regulated | Mitochondrial carrier family | NO | YES | | |
| Spipo13G0011300 | 4 | 3034.8 | 676.8 | down-regulated | Ferredoxin I | NO | NO | | |
| Spipo9G0063000 | 4 | 13.1 | 2.9 | down-regulated | Beta-galactosidase | NO | YES | | |
| Spipo3G0083800 | 4 | 297.7 | 66.7 | down-regulated | Bifunctional inhibitor/lipid-transfer protein/seed storage 2S albumin superfamily | NO | NO | | |
| Spipo29G0021000 | 4 | 61.1 | 14.2 | down-regulated | PsbP-like protein 2 | NO | YES | | |
| Spipo2G0055800 | 4 | 17.1 | 4.0 | down-regulated | bZIP transcription factor I | NO | YES | | |
| Spipo3G0101700 | 4 | 12.6 | 3.0 | down-regulated | Receptor kinase | NO | YES | | |
| Spipo29G0004100 | 4 | 288.3 | 68.2 | down-regulated | unknown protein | NO | YES | | |
| Spipo11G0012500 | 4 | 104.1 | 24.7 | down-regulated | Antiholin-like protein LrgB | NO | NO | | |

TABLE S1-continued

| Gene ID | Fold change | Frond FPKM | Turion FPKM | Directionality | Annotation | ABRE | ERE | GO | Function |
|---|---|---|---|---|---|---|---|---|---|
| Spipo11G0008200 | 4 | 1110.6 | 266.8 | down-regulated | Acyl-CoA-binding protein | NO | YES | | |
| Spipo9G0043500 | 4 | 42.3 | 10.2 | down-regulated | Phosphatidylinositol transfer protein SFH5 | YES | YES | | |
| Spipo23G0035900 | 4 | 68.8 | 16.6 | down-regulated | Omega-3 fatty acid desaturase | NO | YES | | |
| Spipo27G0016000 | 4 | 50.1 | 12.1 | down-regulated | Ubiquitin-conjugating enzyme E2 C, putative | NO | NO | | |
| Spipo7G0026400 | 4 | 32.6 | 7.9 | down-regulated | DNA-3-methyladenine glycosylase | NO | YES | | |
| Spipo20G0006200 | 4 | 7376.0 | 1797.6 | down-regulated | Acyl-CoA dehydrogenase | NO | NO | | |
| Spipo9G0025800 | 4 | 15.7 | 3.9 | down-regulated | D-arabinono-1,4-lactone oxidase-like protein | NO | YES | | |
| Spipo0G0009000 | 4 | 40.9 | 10.2 | down-regulated | Fructose-bisphosphatealdolase | NO | YES | | |
| Spipo4G0036100 | 4 | 49.7 | 12.3 | down-regulated | Pectatelyase | NO | NO | | |
| Spipo11G0009400 | 4 | 38.9 | 9.7 | down-regulated | Mitochondrial carrier protein | NO | NO | | |

TABLE S2

| Pathway | Gene ID | Enzyme | FPKM in frond | FPKM in turion | Average FPKM in frond | Average FPKM in turion |
|---|---|---|---|---|---|---|
| Lignin | Spipo0G0185100 | CCR1 | 32.6 | 23.5 | 23 | 41 |
| | Spipo11G0026200 | CCR2 | 3.4 | 10.2 | | |
| | Spipo6G0037000 | CCR3 | 45.3 | 35.5 | | |
| | Spipo28G0002300 | CCR4 | 1.0 | 0.9 | | |
| | Spipo23G0040600 | CCR5 | 6.7 | 16.7 | | |
| | Spipo11G0026400 | CCR6 | 5.3 | 10.8 | | |
| | Spipo10G0016700 | CCR7 | 0.3 | 0.6 | | |
| | Spipo10G0000200 | CCR8 | 26.2 | 167.8 | | |
| | Spipo8G0071400 | CCR9 | 20.0 | 24.2 | | |
| | Spipo5G0064600 | CCR10 | 16.7 | 18.6 | | |
| | Spipo7G0010700 | CCR11 | 10.1 | 64.8 | | |
| | Spipo0G0172200 | CCR12 | 215.3 | 306.7 | | |
| | Spipo7G0010800 | CCR13 | 0.4 | 1.4 | | |
| | Spipo14G0054900 | CCR14 | 2.0 | 9.9 | | |
| | Spipo12G0004300 | CAD1 | 18.1 | 32.5 | | |
| | Spipo17G0012300 | CAD2 | 10.8 | 7.8 | | |
| | Spipo1G0069500 | CAD3 | 2.6 | 0.7 | | |
| | Spipo2G0124600 | CAD4 | 3.9 | 2.3 | | |
| Starch | Spipo28G0001400 | APS1 | 264.1 | 242.5 | 70 | 86 |
| | Spipo3G0049000 | APL1 | 127.9 | 18.6 | | |
| | Spipo6G0024200 | APL2 | 23.1 | 34.2 | | |
| | Spipo18G0038500 | APL3 | 36.0 | 291.5 | | |
| | Spipo26G0026900 | SSI | 21.7 | 28.6 | | |
| | Spipo0G0050800 | SSII | 3.4 | 1.6 | | |
| | Spipo14G0048800 | SSIII | 33.4 | 24.0 | | |
| | Spipo14G0042000 | SSIV | 45.7 | 15.6 | | |
| | Spipo1G0057900 | GBSSI | 327.8 | 333.2 | | |
| | Spipo1G0057400 | BEI | 19.6 | 10.3 | | |
| | Spipo0G0008100 | BEII | 40.8 | 72.0 | | |
| | Spipo12G0062400 | ISA1 | 2.8 | 14.6 | | |
| | Spipo3G0051400 | ISA2 | 8.1 | 12.9 | | |
| | Spipo20G0022100 | ISA3 | 25.1 | 98.0 | | |
| Lipid | Spipo0G0127900 | ACCase1 | 24.0 | 17.4 | 28 | 22 |
| | Spipo10G0023400 | ACCase2 | 6.3 | 4.6 | | |
| | Spipo12G0034900 | ACCase3 | 4.5 | 2.5 | | |
| | Spipo12G0063600 | ACCase4 | 85.6 | 44.3 | | |
| | Spipo15G0009000 | ACCase5 | 22.4 | 21.4 | | |
| | Spipo4G0043600 | ACCase6 | 20.9 | 11.0 | | |
| | Spipo4G0047600 | ACCase7 | 73.7 | 56.7 | | |
| | Spipo30G0006700 | GPAT1 | 127.7 | 52.2 | | |
| | Spipo7G0013300 | GPAT2 | 21.0 | 20.4 | | |
| | Spipo3G0111400 | AGPAT1 | 1.4 | 0.3 | | |
| | Spipo4G0068200 | AGPAT2 | 17.6 | 18.2 | | |
| | Spipo6G0030100 | AGPAT3 | 15.8 | 13.5 | | |
| | Spipo7G0018900 | AGPAT4 | 4.3 | 3.3 | | |
| | Spipo7G0051900 | AGPAT5 | 1.6 | 0.9 | | |
| | Spipo21G0027500 | DGAT1 | 6.0 | 5.7 | | |

TABLE S2-continued

| Pathway | Gene ID | Enzyme | FPKM in frond | FPKM in turion | Average FPKM in frond | Average FPKM in turion |
|---|---|---|---|---|---|---|
| | Spipo28G0006400 | DGAT2 | 70.9 | 117.6 | | |
| | Spipo1G0066600 | DGAT3 | 0.9 | 1.5 | | |
| | Spipo20G0011900 | DGAT4 | 11.2 | 8.2 | | |
| | Spipo3G0079500 | DGAT5 | 14.6 | 23.1 | | |

The data presented in Table S2 reveal suitable targets for altering carbon partitioning in duckweed. For example, reducing expression of GPAT1 in fronds should increase protein content in duckweed cells. In another approach, introduction of a LEA promoter operably linked to an agent (e.g., an siRNA) to APL1 should increase the lipid content of in the resulting duckweed culture. In yet another approach, one could simultaneously target two or more genes in duckweed which are differentially expressed to alter carbon partitioning in the resulting cells. Methods for introducing transgenes into Duckweed are described in Canto-Pastor, A., Mollá, Morales, A., Ernst, E., Dahl, W., Zhai, J., Yan, Y., Meyers, B. C., Shanklin, J., Martienssen, R. (2014), Efficient transformation and artificial miRNA gene silencing in *Lemna minor*. Plant Biology. doi: 10.1111/plb.12215. Sequence information is available on the world wide web at Waksman.rutgers.edu/spirodela/genome.

REFERENCES

1. Jones S I, Vodkin L O: Using RNA-Seq to profile soybean seed development from fertilization to maturity. *PLoS One* 2013, 8(3):e59270.
2. Bentsink L, Hanson J, Hanhart C J, Blankestijn-de Vries H, Coltrane C, Keizer P, El-Lithy M, Alonso-Blanco C, de Andres M T, Reymond M et al: Natural variation for seed dormancy in *Arabidopsis* is regulated by additive genetic and molecular pathways. *Proc Natl Acad Sci USA* 2010, 107(9):4264-4269.
3. Liu A, Gao F, Kanno Y, Jordan M C, Kamiya Y, Seo M, Ayele B T: Regulation of wheat seed dormancy by afterripening is mediated by specific transcriptional switches that induce changes in seed hormone metabolism and signaling. *PLoS One* 2013, 8(2):e56570.
4. Vegis A: Dormancy in Higher Plants. *Annual Review of Plant Physiology* 1964, 15(1):185-224.
5. Liu G, Li W, Zheng P, Xu T, Chen L, Liu D, Hussain S, Teng Y: Transcriptomic analysis of 'Suli' pear (*Pyrus pyrifolia* white pear group) buds during the dormancy by RNA-Seq. *BMC Genomics* 2012, 13:700.
6. Ueno S, Klopp C, Leple J C, Derory J, Noirot C, Leger V, Prince E, Kremer A, Plomion C, Le Provost G: Transcriptional profiling of bud dormancy induction and release in oak by next-generation sequencing. *BMC Genomics* 2013, 14:236.
7. Ruttink T, Arend M, Morreel K, Storme V, Rombauts S, Fromm J, Bhalerao R P, Boerjan W, Rohde A: A molecular timetable for apical bud formation and dormancy induction in poplar. *Plant Cell* 2007, 19(8):2370-2390.
8. Landolt E: The family of Lemnaceae—a monographic study, Vols. 1: Veroffentlichungen des Geobotanischen Institutes der Eidgenossischen Technischen Hochschule, Stiftung Rubel; 1986.
9. Appenroth K-J, Nickel G: Turion formation in *Spirodela polyrhiza*: The environmental signals that induce the developmental process in nature. *Physiologia Plantarum* 2009, 138(3):312-320.
10. Appenroth K J, Teller S, Horn M: Photophysiology of turion formation and germination in *Spirodela polyrhiza*. *Biologia Plantarum* 1996, 38(1):95-106.
11. Appenroth K J, Ziegler P: Light-induced degradation of storage starch in turions of *Spirodela polyrhiza* depends on nitrate. *Plant Cell Environ* 2008, 31(10):1460-1469.
12. Appenroth K J, Keresztes A, Krzysztofowicz E, Gabrys H: Light-induced degradation of starch granules in turions of *Spirodela polyrhiza* studied by electron microscopy. *Plant Cell Physiol* 2011, 52(2):384-391.
13. Wang W, Messing J: Analysis of ADP-glucose pyrophosphorylase expression during turion formation induced by abscisic acid in *Spirodela polyrhiza* (greater duckweed). *BMC Plant Biol* 2012, 12:5.
14. Smart C C, Trewavas A J: Abscisic-acid-induced turion formation in *Spirodela polyrrhiza* L. II. Ultrastructure of the turion; a stereological analysis. *Plant, Cell and Environment* 1983, 6(6):515-522.
15. Smart C C, Trewavas A J: Abscisic-acid-induced turion formation in *Spirodela polyrrhiza* L. I. Production and development of the turion. *Plant, Cell and Environment* 1983, 6(6):507-514.
16. Smart C C, Fleming A J, Chaloupkova K, Hanke D E: The physiological role of abscisic acid in eliciting turion morphogenesis. *Plant Physiol* 1995, 108(2):623-632.
17. Plant dormancy: physiology, biochemistry and molecular biology. In: 1996; Wallingford: CAB INTERNATIONAL; 1996: xx+386 pp.
18. Smart C C, Fleming A J: A plant gene with homology to D-myo-inositol-3-phosphate synthase is rapidly and spatially up-regulated during an abscisic-acid-induced morphogenic response in *Spirodela polyrrhiza*. *Plant J* 1993, 4(2):279-293.
19. Flores S, Smart C C: Abscisic acid-induced changes in inositol metabolism in *Spirodela polyrrhiza*. *Planta* 2000, 211(6):823-832.
20. Wu Y, Messing J: RNA interference-mediated change in protein body morphology and seed opacity through loss of different zein proteins. *Plant Physiol* 2010, 153(1):337-347.
21. Trapnell C, Pachter L, Salzberg S L: TopHat: discovering splice junctions with RNA-Seq. *Bioinformatics* 2009, 25(9):1105-1111.
22. Langmead B, Salzberg S L: Fast gapped-read alignment with Bowtie 2. *Nat Methods* 2012, 9(4):357-359.
23. Trapnell C, Roberts A, Goff L, Pertea G, Kim D, Kelley D R, Pimentel H, Salzberg S L, Rinn J L, Pachter L: Differential gene and transcript expression analysis of RNA-seq experiments with TopHat and Cufflinks. *Nat Protoc* 2012, 7(3):562-578.
24. Chaloupkova K, Smart C C: The abscisic acid induction of a novel peroxidase is antagonized by cytokinin in *Spirodela polyrrhiza* L. *Plant Physiol* 1994, 105(2):497-507.
25. Conesa A, Gotz S, Garcia-Gomez J M, Terol J, Talon M, Robles M: Blast2GO: a universal tool for annotation, visualization and analysis in functional genomics research. *Bioinformatics* 2005, 21(18):3674-3676.
26. Young M D, Wakefield M J, Smyth G K, Oshlack A: Gene ontology analysis for RNA-seq: accounting for selection bias. *Genome Biol* 2010, 11(2):R14.
27. Higo K, Ugawa Y, Iwamoto M, Korenaga T: Plant cis-acting regulatory DNA elements (PLACE) database: 1999. *Nucleic Acids Res* 1999, 27(1):297-300.
28. Smart C C, Trewavas A J: Abscisic-acid-induced turion formation in *Spirodela polyrrhiza* L III. Specific changes in protein synthesis and translatable RNA during turion development. *Plant, Cell and Environment* 1984, 7(2): 121-132.
29. Smart C C, Trewavas A J: Abscisic-acid-induced turion formation in *Spirodela polyrrhiza* L. IV. Comparative ion flux characteristics of the turion and the vegetative frond and the effect of ABA during early turion development. *Plant, Cell and Environment* 1984, 7(7):521-530.
30. Wang W, Messing J: High-Throughput Sequencing of Three Lemnoideae (Duckweeds) Chloroplast Genomes from Total DNA. *PLoS ONE* 2011, 6(9):e24670.
31. Wang W, Wu Y, Messing J: The mitochondrial genome of an aquatic plant, *Spirodela polyrhiza*. *PLoS One* 2012, 7(10):e46747.
32. Wang W, Haberer, G., Gundlach, H., Gläβer, C., Nussbaumer, T., Luo, M.-C., Lomsadze, A., Borodovsky, M., Kerstetter, R. A., Shanklin, J., Byrant D., Mockler, T., Appenroth, K. J., Grimwood, J., Jenkins, J., Chow, J., Choi, C., Adam, C., Cao, X H., Fuchs, J., Schubert, I., Rokhsar, D., Schmutz, J., Michael, T. P., Mayer, K. F. X., and Messing, J.: Reduced gene content in the genome of Greater Duckweed reflects essentials in plant morphogenesis. Submitted 2013.
33. Smith D R: RNA-Seq data: a goldmine for organelle research. *Brief Funct Genomics* 2013.
34. Xu H, Gao Y, Wang J: Transcriptomic analysis of rice (*Oryza sativa*) developing embryos using the RNA-Seq technique. *PLoS One* 2012, 7(2):e30646.
35. Kakumanu A, Ambavaram M M, Klumas C, Krishnan A, Batlang U, Myers E, Grene R, Pereira A: Effects of drought on gene expression in maize reproductive and leaf meristem tissue revealed by RNA-Seq. *Plant Physiol* 2012, 160(2):846-867.
36. Socquet-Juglard D, Kamber T, Pothier J F, Christen D, Gessler C, Duffy B, Patocchi A: Comparative RNA-seq analysis of early-infected peach leaves by the invasive phytopathogen *Xanthomonas arboricola* pv. *pruni*. *PLoS One* 2013, 8(1):e54196.
37. Raz T, Kapranov P, Lipson D, Letovsky S, Milos P M, Thompson J F: Protocol dependence of sequencing-based gene expression measurements. *PLoS One* 2011, 6(5): e19287.
38. Hansen K D, Wu Z, Irizarry R A, Leek J T: Sequencing technology does not eliminate biological variability. *Nat Biotechnol* 2011, 29(7):572-573.
39. Fang Z, Cui X: Design and validation issues in RNA-seq experiments. *Brief Bioinform* 2011, 12(3):280-287.
40. Kvam V M, Liu P, Si Y: A comparison of statistical methods for detecting differentially expressed genes from RNA-seq data. *Am J Bot* 2012, 99(2):248-256.
41. Robles J A, Qureshi S E, Stephen S J, Wilson S R, Burden C J, Taylor J M: Efficient experimental design and analysis strategies for the detection of differential expression using RNA-Sequencing. *BMC Genomics* 2012, 13:484.
42. Christmann A, Moes D, Himmelbach A, Yang Y, Tang Y, Grill E: Integration of abscisic acid signalling into plant responses. *Plant Biol* (Stuttg) 2006, 8(3):314-325.
43. Rodriguez-Gacio Mdel C, Matilla-Vazquez M A, Matilla A J: Seed dormancy and ABA signaling: the breakthrough goes on. *Plant Signal Behav* 2009, 4(11):1035-1049.
44. Finkelstein R R, Gampala S S, Rock C D: Abscisic acid signaling in seeds and seedlings. *Plant Cell* 2002, 14 Suppl:S15-45.
45. Chen J, Huang B, Li Y, Du H, Gu Y, Liu H, Zhang J, Huang Y: Synergistic influence of sucrose and abscisic acid on the genes involved in starch synthesis in maize endosperm. *Carbohydr Res* 2011, 346(13):1684-1691.
46. Cosgrove D J: Loosening of plant cell walls by expansins. *Nature* 2000, 407(6802):321-326.
47. Reisen D, Leborgne-Castel N, Ozalp C, Chaumont F, Marty F: Expression of a cauliflower tonoplast aquaporin tagged with GFP in tobacco suspension cells correlates with an increase in cell size. *Plant Mol Biol* 2003, 52(2):387-400.
48. Lin W, Peng Y, Li G, Arora R, Tang Z, Su W, Cai W: Isolation and functional characterization of PgTIP1, a hormone-autotrophic cells-specific tonoplast aquaporin in ginseng. *J Exp Bot* 2007, 58(5):947-956.
49. Hundertmark M, Hincha D K: LEA (late embryogenesis abundant) proteins and their encoding genes in *Arabidopsis thaliana*. *BMC Genomics* 2008, 9:118.
50. Espelund M, Saeboe-Larssen S, Hughes D W, Galau G A, Larsen F, Jakobsen K S: Late embryogenesis-abundant genes encoding proteins with different numbers of hydrophilic repeats are regulated differentially by abscisic acid and osmotic stress. *Plant J* 1992, 2(2):241-252.
51. Ried J L, Walker-Simmons M K: Group 3 Late Embryogenesis Abundant Proteins in Desiccation-Tolerant Seedlings of Wheat (*Triticum aestivum* L.). *Plant Physiol* 1993, 102(1):125-131.
52. Rook F, Corke F, Card R, Munz G, Smith C, Bevan M W: Impaired sucrose-induction mutants reveal the modulation of sugar-induced starch biosynthetic gene expression by abscisic acid signalling. *Plant J* 2001, 26(4):421-433.
53. Tao X, Fang Y, Xiao Y, Jin Y L, Ma X R, Zhao Y, He K Z, Zhao H, Wang H Y: Comparative transcriptome analysis to investigate the high starch accumulation of duckweed (*Landoltia punctata*) under nutrient starvation. *Biotechnol Biofuels* 2013, 6(1):72.
54. Ekman A, Hayden D M, Dehesh K, Bulow L, Stymne S: Carbon partitioning between oil and carbohydrates in developing oat (*Avena sativa* L.) seeds. *J Exp Bot* 2008, 59(15):4247-4257.
55. Weselake R J, Taylor D C, Rahman M H, Shah S, Laroche A, McVetty P B, Harwood J L: Increasing the flow of carbon into seed oil. *Biotechnol Adv* 2009, 27(6): 866-878.
56. Jakoby M, Weisshaar B, Droge-Laser W, Vicente-Carbajosa J, Tiedemann J, Kroj T, Parcy F: bZIP transcription factors in *Arabidopsis*. *Trends Plant Sci* 2002, 7(3):106-111.
57. Fujita Y, Fujita M, Shinozaki K, Yamaguchi-Shinozaki K: ABA-mediated transcriptional regulation in response to osmotic stress in plants. *J Plant Res* 2011, 124(4):509-525.
58. Bensmihen S, Rippa S, Lambert G, Jublot D, Pautot V, Granier F, Giraudat J, Parcy F: The homologous ABI5 and EEL transcription factors function antagonistically to fine-tune gene expression during late embryogenesis. *Plant Cell* 2002, 14(6):1391-1403.

59. Fujimoto S Y, Ohta M, Usui A, Shinshi H, Ohme-Takagi M: Arabidopsis ethylene-responsive element binding factors act as transcriptional activators or repressors of GCC box-mediated gene expression. *Plant Cell* 2000, 12(3): 393-404.
60. Riechmann J L, Meyerowitz E M: The AP2/EREBP family of plant transcription factors. *Biol Chem* 1998, 379(6):633-646.
61. El-Sharkawy I, Sherif S, Mila I, Bouzayen M, Jayasankar S: Molecular characterization of seven genes encoding ethylene-responsive transcriptional factors during plum fruit development and ripening. *J Exp Bot* 2009, 60(3):907-922.
62. Ohta M, Ohme-Takagi M, Shinshi H: Three ethylene-responsive transcription factors in tobacco with distinct transactivation functions. *Plant J* 2000, 22(1):29-38.
63. Schoffl F, Prandl R, Reindl A: Regulation of the heat-shock response. *Plant Physiol* 1998, 117(4):1135-1141.
64. Rushton D L, Tripathi P, Rabara R C, Lin J, Ringler P, Boken A K, Langum T J, Smidt L, Boomsma D D, Emme N J et al: WRKY transcription factors: key components in abscisic acid signalling. *Plant Biotechnol J* 2012, 10(1): 2-11.
65. Antoni R, Rodriguez L, Gonzalez-Guzman M, Pizzio G A, Rodriguez P L: News on ABA transport, protein degradation, and ABFs/WRKYs in ABA signaling. *Curr Opin Plant Biol* 2011, 14(5):547-553.
66. Himmelbach A, Yang Y, Grill E: Relay and control of abscisic acid signaling. *Curr Opin Plant Biol* 2003, 6(5): 470-479.
67. Lang G A: Plant dormancy: physiology, biochemistry and molecular biology: CAB International; 1996.
68. Webb A A, Larman M G, Montgomery L T, Taylor J E, Hetherington A M: The role of calcium in ABA-induced gene expression and stomatal movements. *Plant J* 2001, 26(3):351-362.
69. Cheng S H, Willmann M R, Chen H C, Sheen J: Calcium signaling through protein kinases. The *Arabidopsis* calcium-dependent protein kinase gene family. *Plant Physiol* 2002, 129(2):469-485.
70. Stomp A M: The duckweeds: a valuable plant for biomanufacturing. *Biotechnol Annu Rev* 2005, 11:69-99.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A method for altering carbon partitioning from starch to lipids in biomass produced from Duckweed cultures, comprising introducing a transgene comprising a LEA (late embryogenesis abundant protein) promoter operably linked to at least one sequence encoding an RNA interference product targeting a gene selected from APL1, APL2, and APL3, and/or a transgene comprising an LEA promoter operably linked to at least one coding region for a gene selected from the group consisting of ACCase1, ACCase2, ACCase3, ACCase4, ACCase5, ACCase6, and ACCase7, wherein expression of said transgene or transgenes is effective to reduce starch production and increase lipid production in said culture relative to control untreated cultures.

2. The method of claim 1, wherein introduction of said transgene results in increased lipid production in biomass obtained from said Duckweed culture.

3. The method of claim 2, wherein said transgene is an RNAi and inhibits expression of at least one gene selected from the group consisting of APL1, APL2, and APL3.

4. A Duckweed plant produced from the method of claim 1, wherein the Duckweed plant comprises a transgene comprising a LEA promoter operably linked to at least one sequence encoding an RNA interference product targeting a gene selected from APL1, APL2, and APL3, and, or a transgene comprising a LEA promoter operably linked to at least one coding region for a gene selected from the group consisting of ACCase1, ACCase2, ACCase3, ACCase4, ACCase5, ACCase6, and ACCase7.

5. The Duckweed plant of claim 4, which is *Spirodela polyrhiza*.

6. A plant part, progeny, seed or cell obtained from the plant of claim 5.

7. A method for altering carbon partitioning from starch to lipids in biomass produced from duckweed cultures comprising introducing a transgene comprising a LEA promoter operably linked to an siRNA targeting the APL3 gene and culturing said duckweed under conditions promoting turion formation, said transgene causing a decrease in APL3 expression, thereby increasing lipid content of said cultures relative to control untreated cultures.

8. A transgenic duckweed as claimed in claim 7.

9. The duckweed plant of claim 8, which is *Spirodela polyrhiza*.

10. A plant part, progeny, seed or cell obtained from the plant of claim 9.

* * * * *